United States Patent
Hatta et al.

[11] Patent Number: 5,931,836
[45] Date of Patent: Aug. 3, 1999

[54] ELECTROSURGERY APPARATUS AND MEDICAL APPARATUS COMBINED WITH THE SAME

[75] Inventors: Shinji Hatta, Hachioji; Masakazu Gotanda, Kanagawa-ken; Tomohisa Sakurai, Sagamihara; Yoshito Ichikawa, Saitama-ken; Kazuya Hijii, Hachioji; Masahide Oyama, Fussa; Takashi Mihori, Sagamihara; Hiroaki Matsumoto, Tokyo; Akihisa Ogawa, Hachioji; Kazue Tanaka, Sagamihara, all of Japan

[73] Assignee: Olympus Optical Co., Ltd., Tokyo, Japan

[21] Appl. No.: 08/896,734

[22] Filed: Jul. 21, 1997

[30] Foreign Application Priority Data

| Jul. 29, 1996 | [JP] | Japan | 8-199190 |
| Jul. 29, 1996 | [JP] | Japan | 8-199191 |
| Dec. 13, 1996 | [JP] | Japan | 8-334123 |
| Jul. 9, 1997 | [JP] | Japan | 9-183744 |
| Jul. 9, 1997 | [JP] | Japan | 9-183748 |

[51] Int. Cl.⁶ ........................................ A61B 17/36
[52] U.S. Cl. .............................. 606/38; 606/34; 606/42; 606/45
[58] Field of Search .................. 606/41–46, 32–39

[56] References Cited

U.S. PATENT DOCUMENTS

| 4,658,819 | 4/1987 | Harris et al. . | |
| 4,785,807 | 11/1988 | Blanch | 606/45 |
| 4,800,878 | 1/1989 | Cartmell | 606/45 |
| 4,961,047 | 10/1990 | Carder . | |
| 4,969,885 | 11/1990 | Farin . | |
| 5,167,658 | 12/1992 | Ensslin . | |
| 5,370,645 | 12/1994 | Klicek et al. . | |
| 5,540,683 | 7/1996 | Ichikawa et al. . | |
| 5,558,671 | 9/1996 | Yates | 606/38 |
| 5,733,281 | 3/1998 | Nardella | 606/38 |

*Primary Examiner*—Michael Buiz
*Assistant Examiner*—Julian W. Woo
*Attorney, Agent, or Firm*—Frishauf, Holtz, Goodman, Langer & Chick

[57] ABSTRACT

In an electrosurgery apparatus for treating a living tissue, while the living tissue is being treated, a variation in state of energy supplied from a cautery power supply to a monopolar treatment device is detected on the basis of detection data obtained from a current sensor and a voltage sensor. Based on the detected variation, living body information on the living tissue to be treated is obtained.

15 Claims, 24 Drawing Sheets

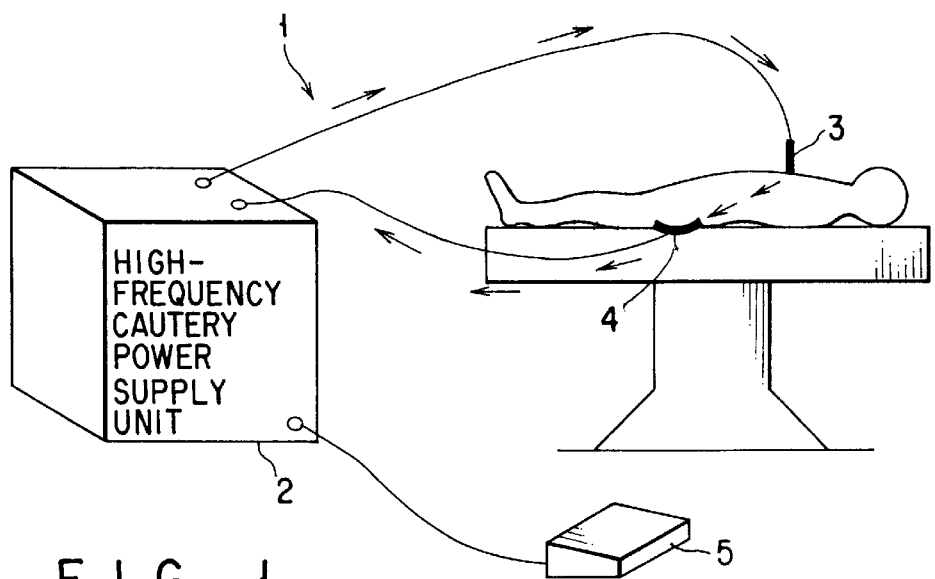
F I G. 1
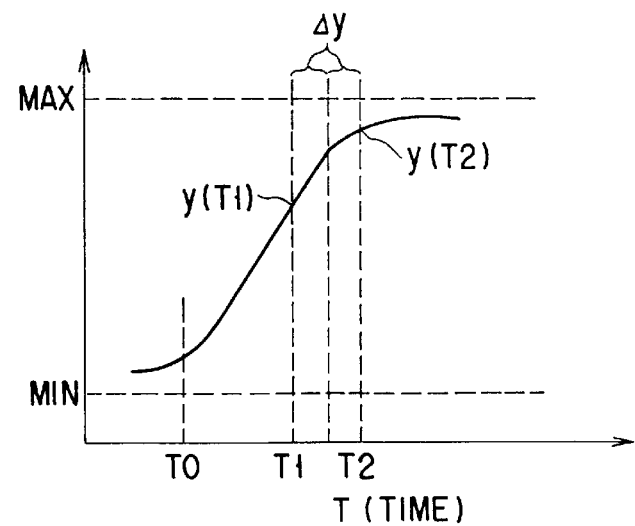
F I G. 3
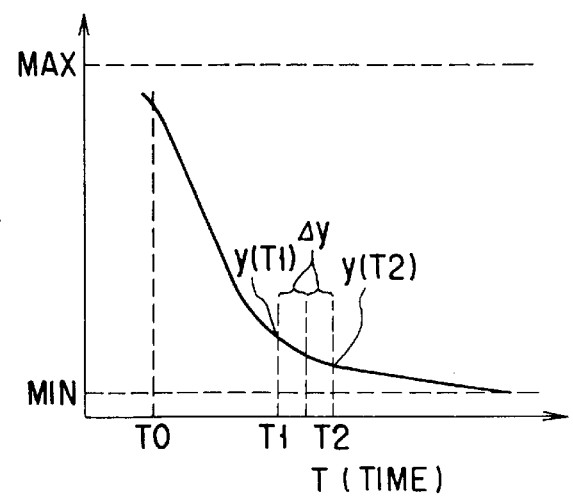
F I G. 4

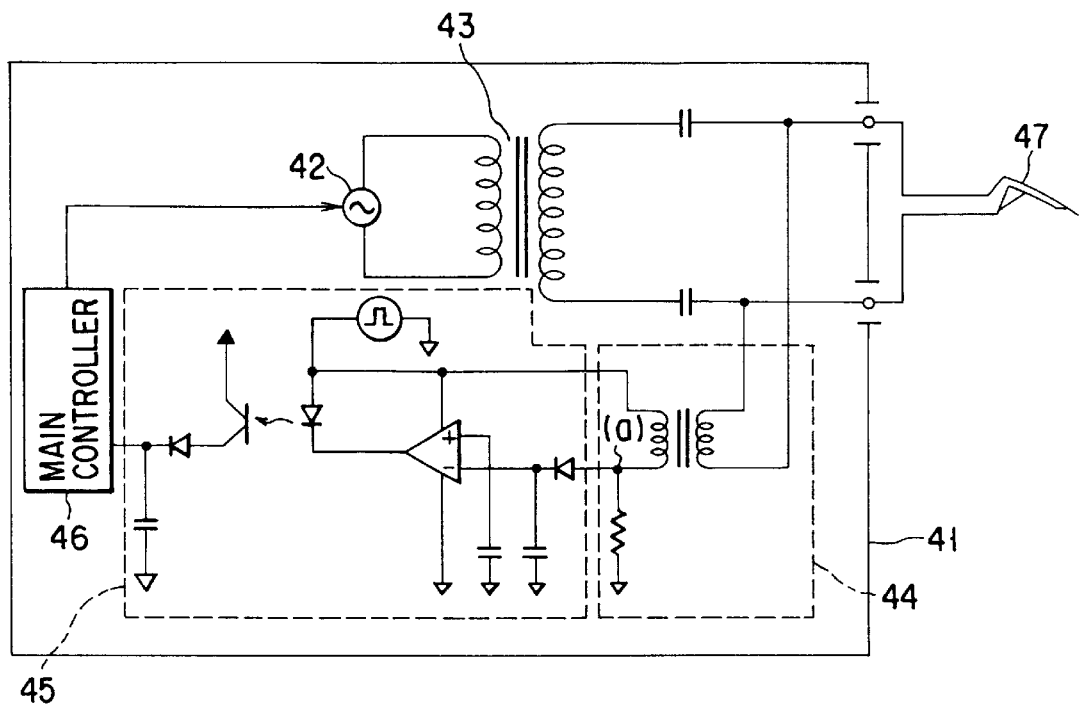
F I G. 11
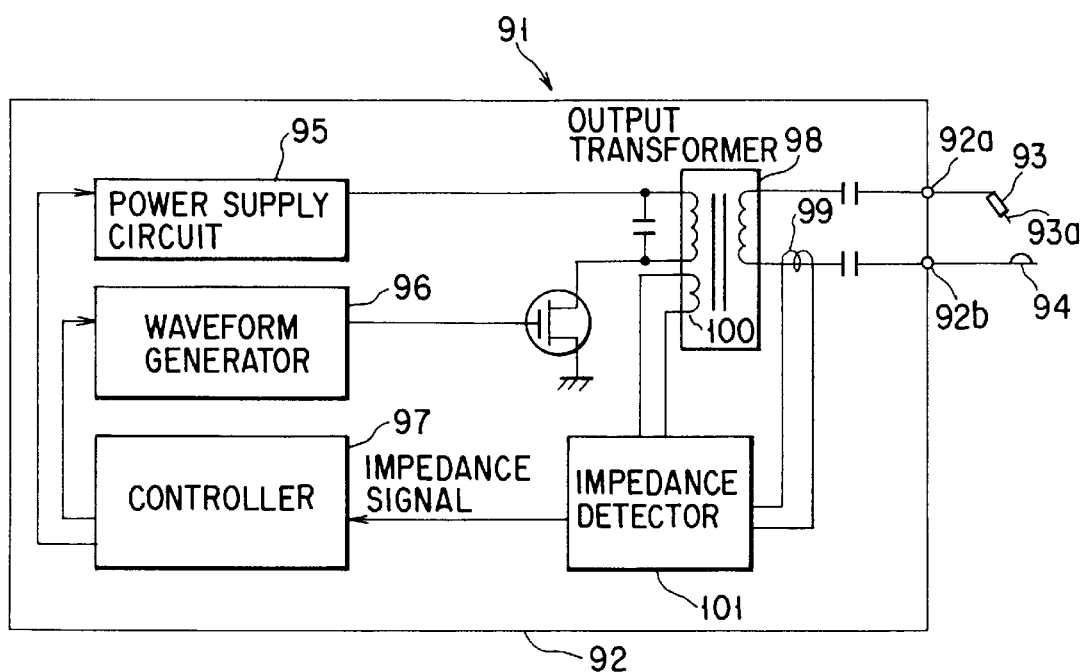
F I G. 12

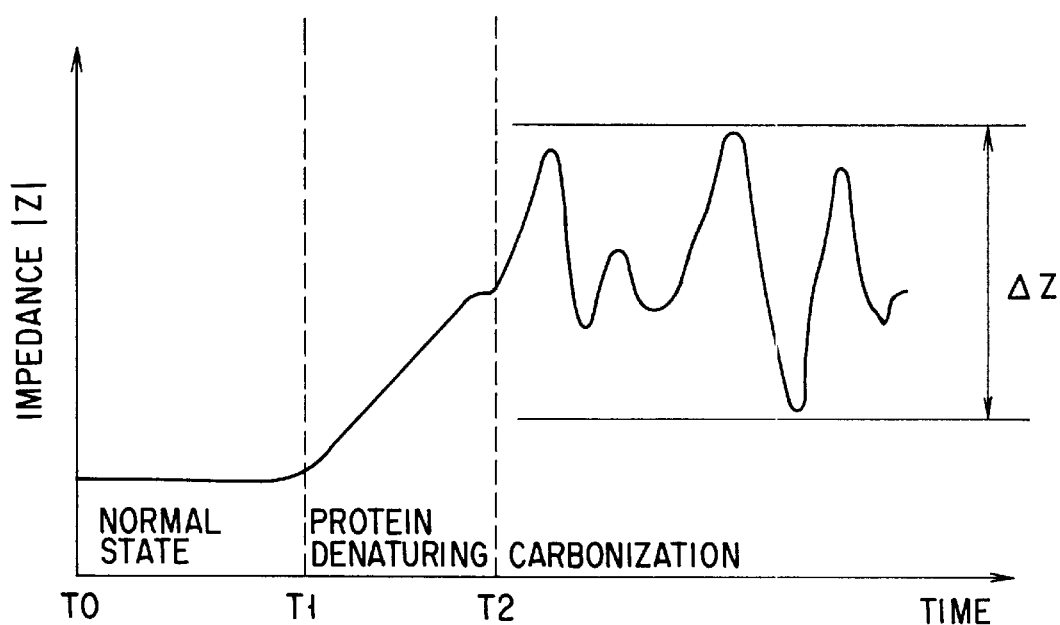
F I G. 13

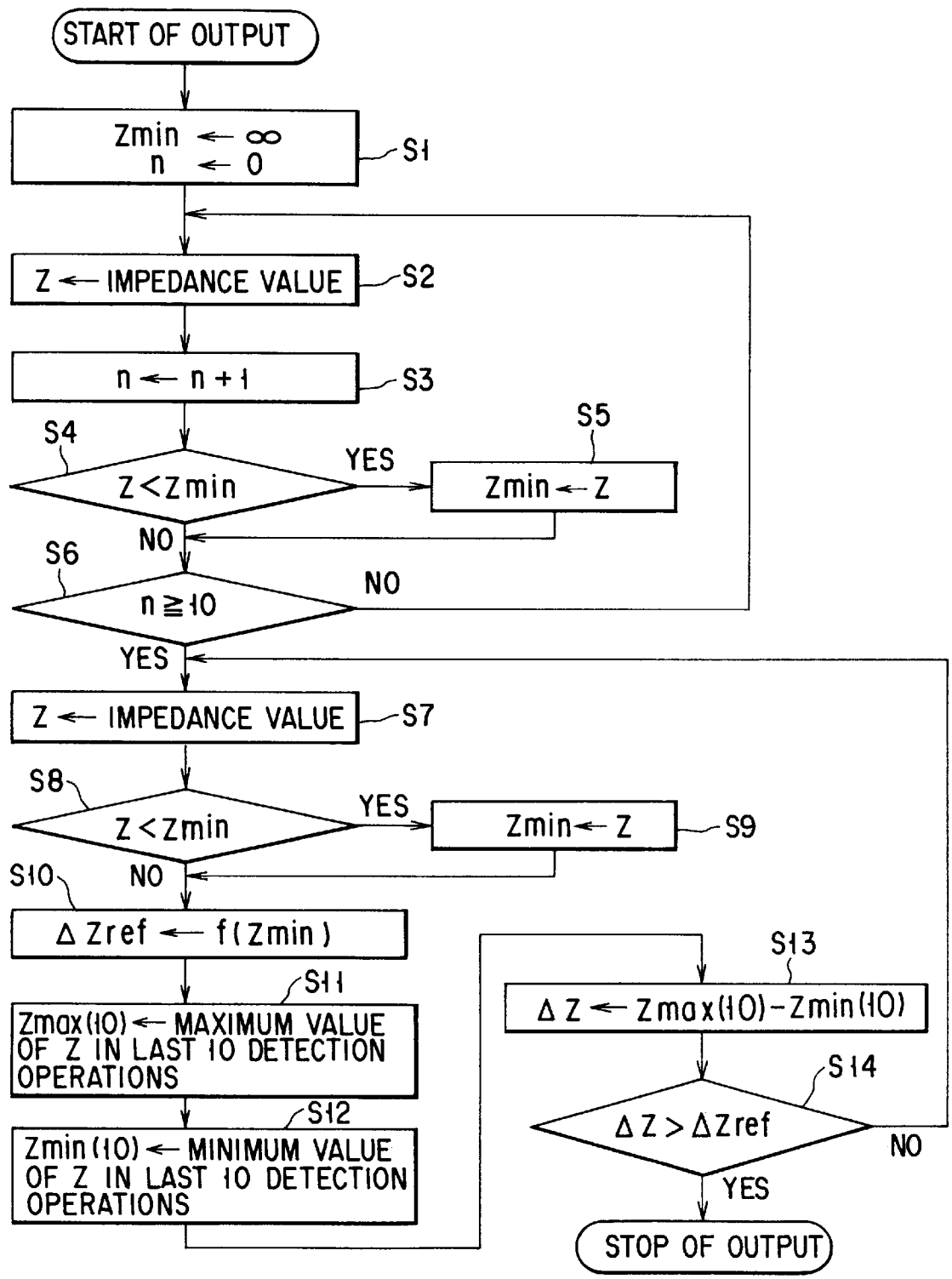
F I G. 14

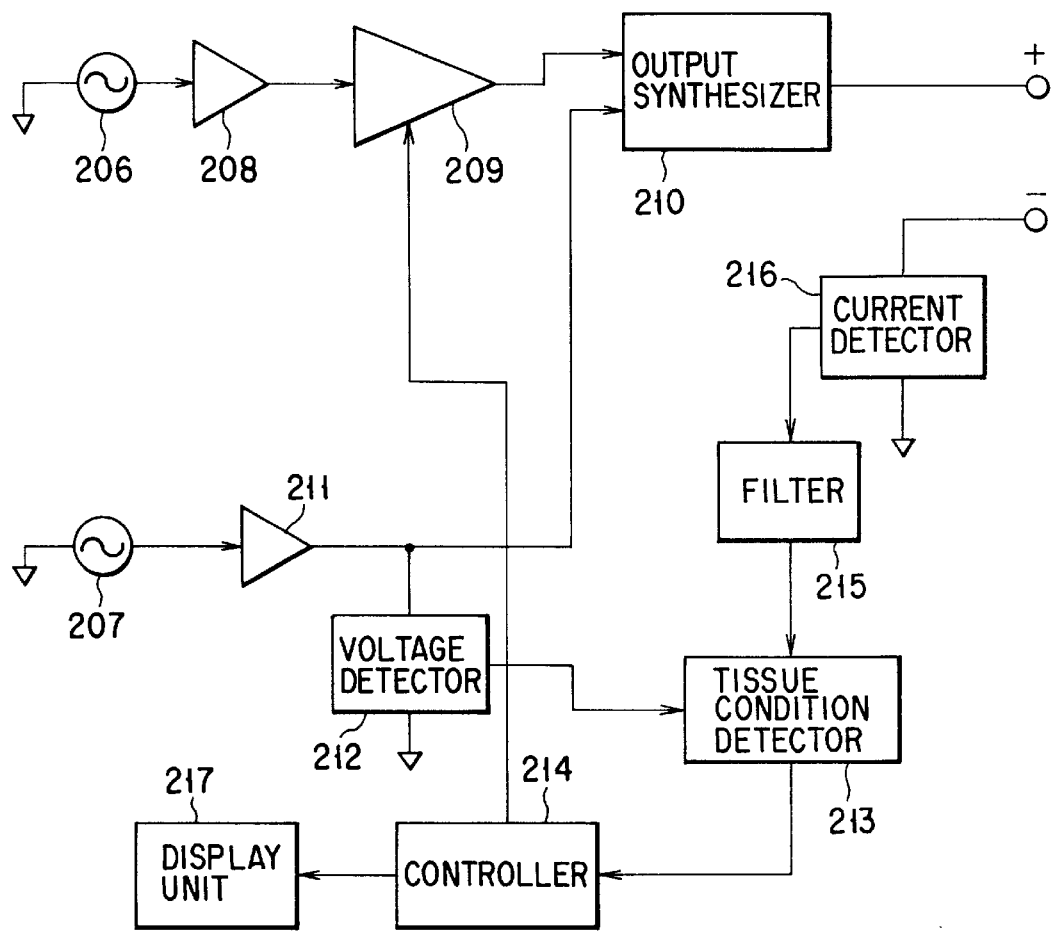
F I G. 20
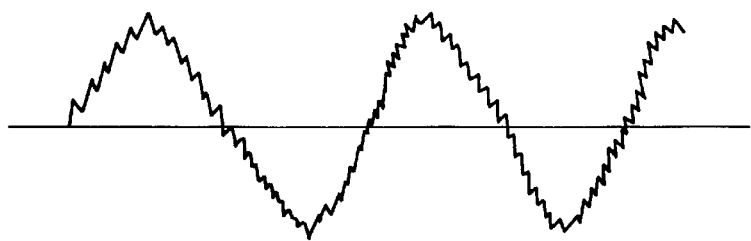
F I G. 21

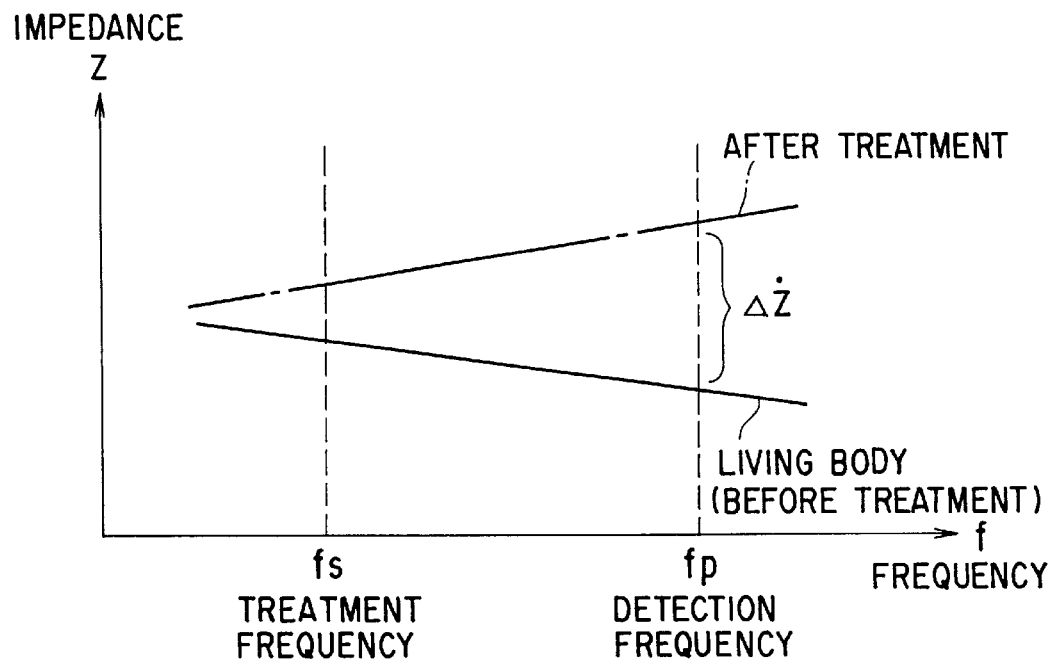
F I G. 22A
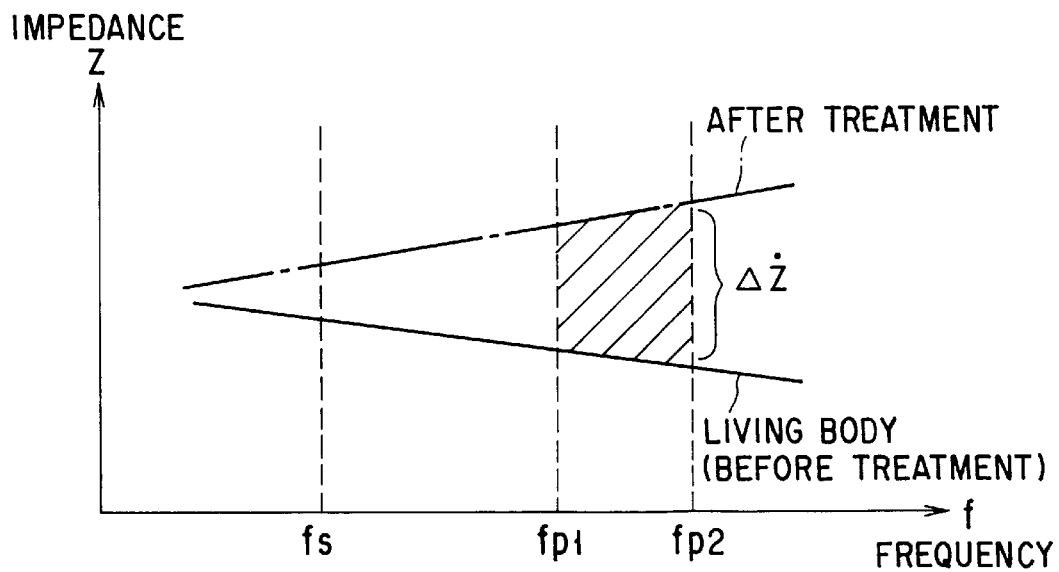
F I G. 22B

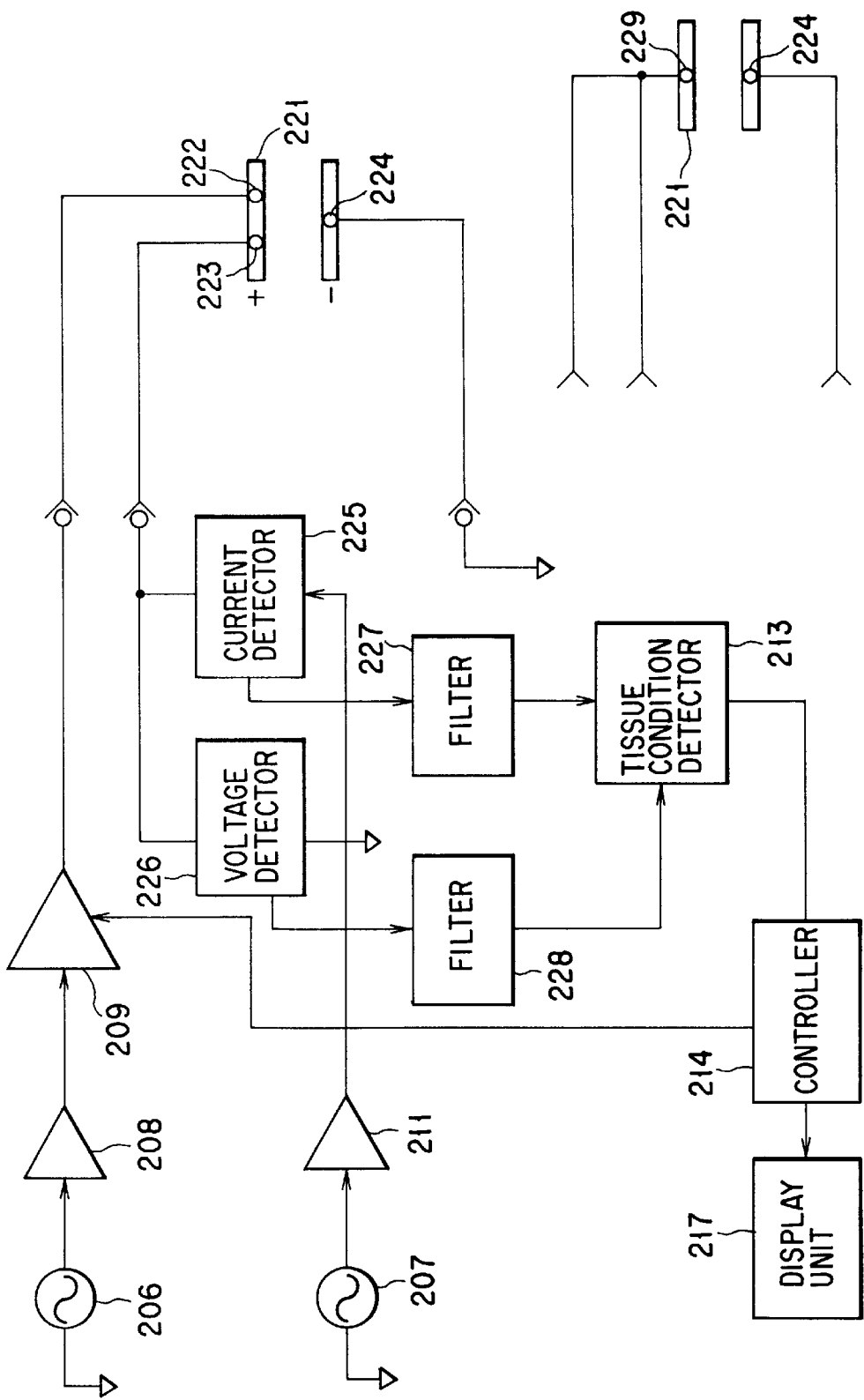

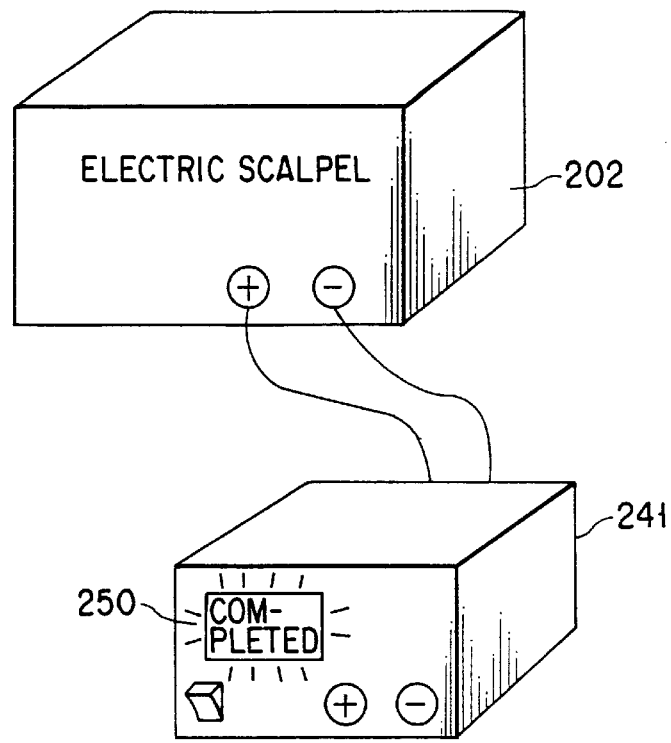
F I G. 26A
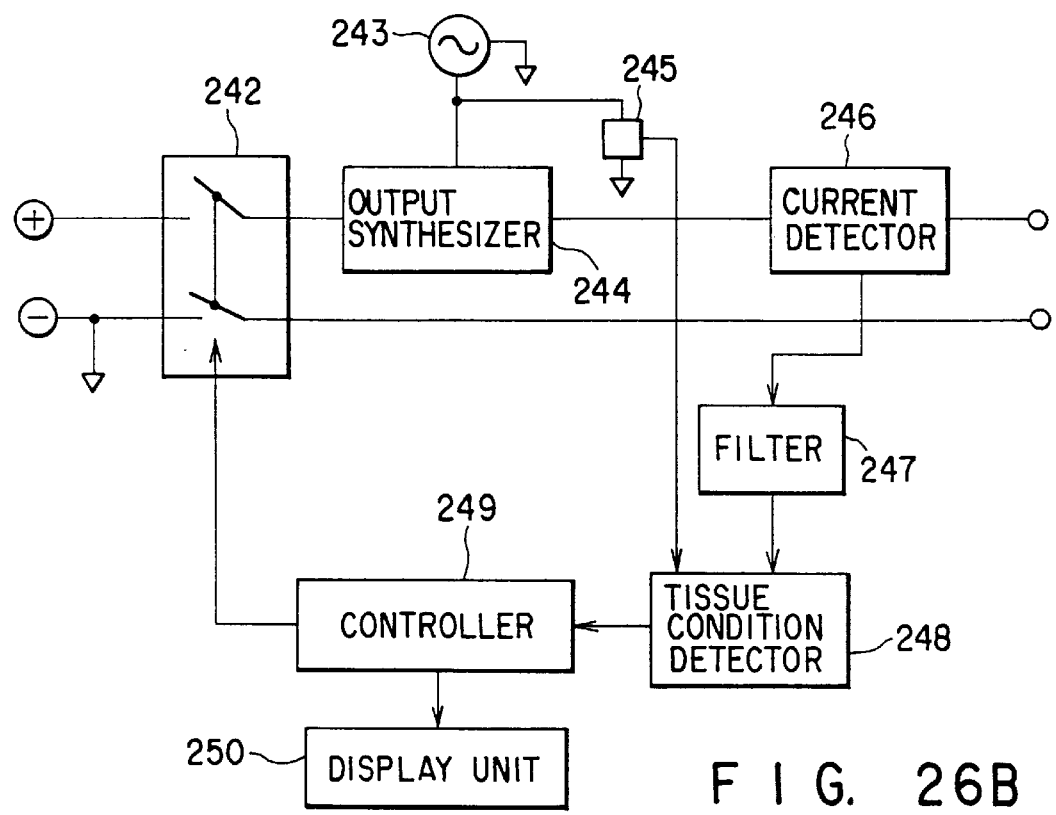
F I G. 26B

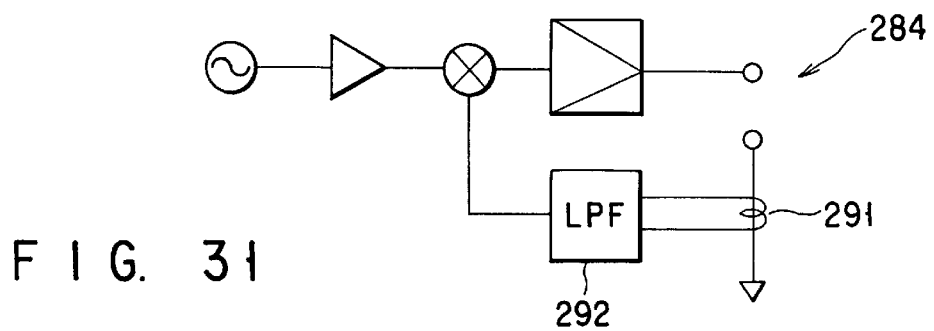
F I G. 31
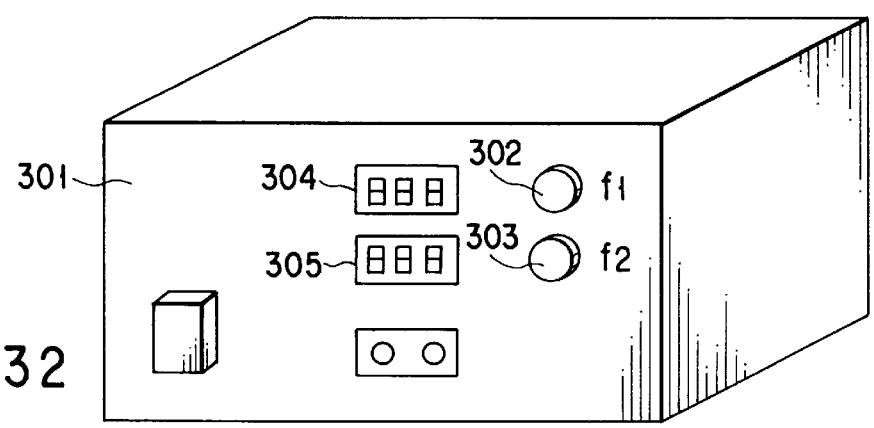
F I G. 32
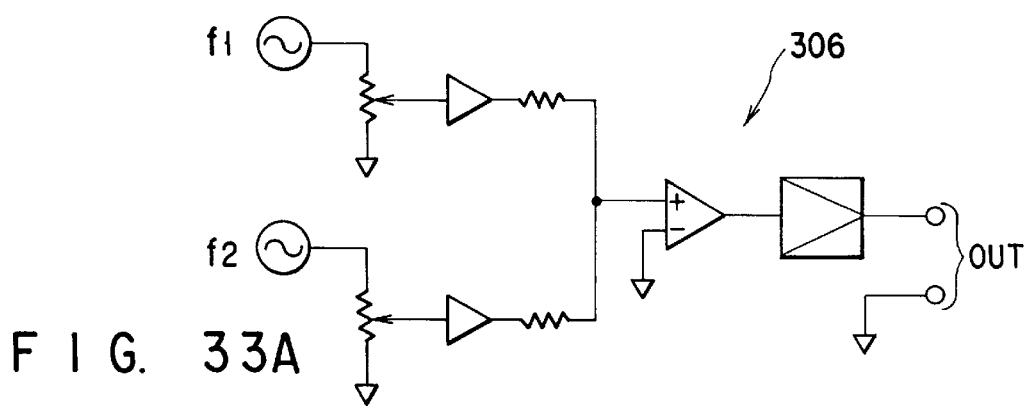
F I G. 33A
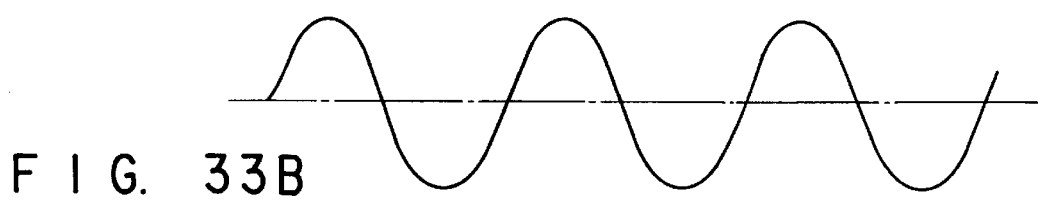
F I G. 33B

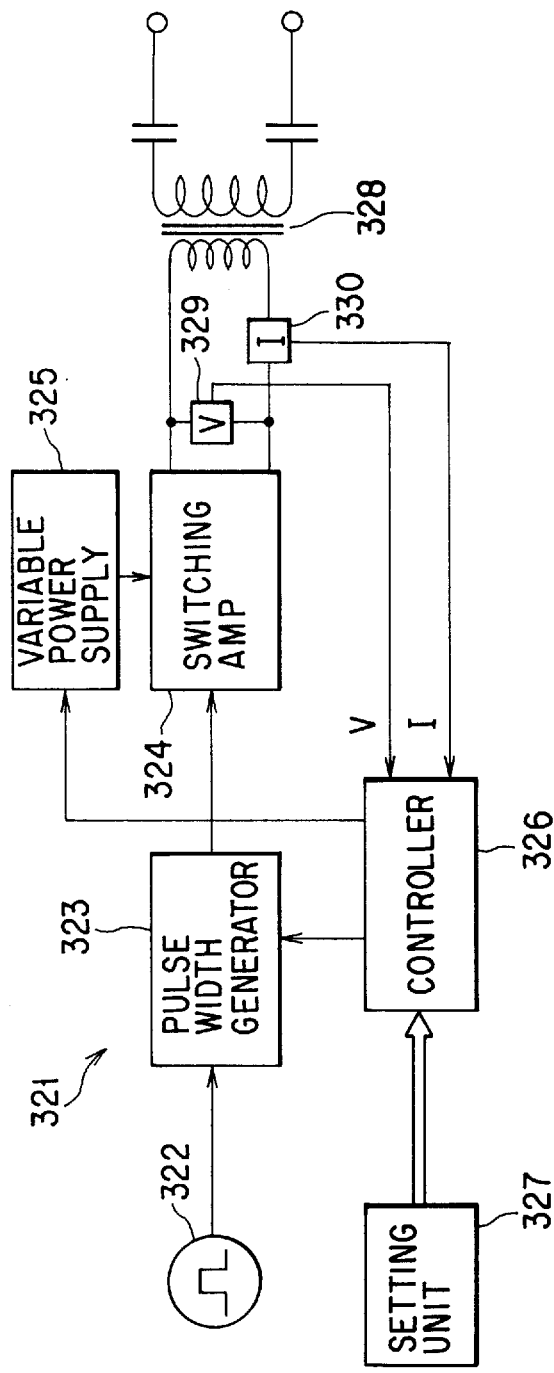
FIG. 34A
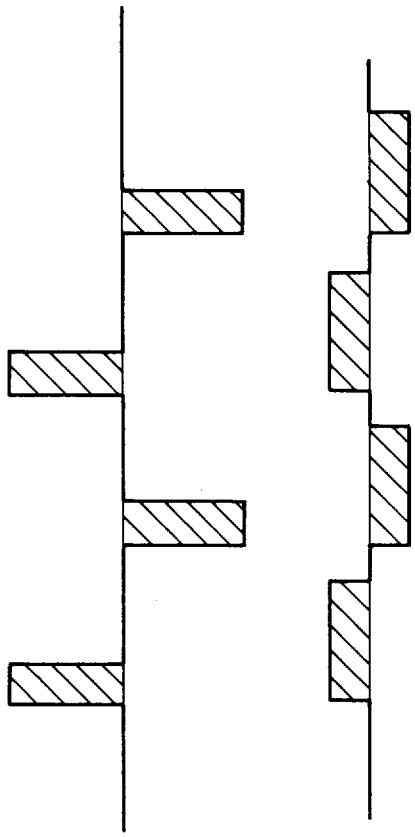
FIG. 34B
FIG. 34C

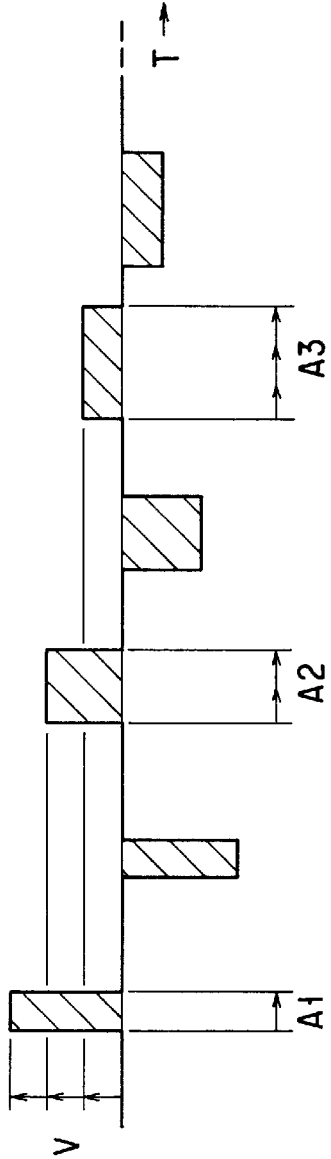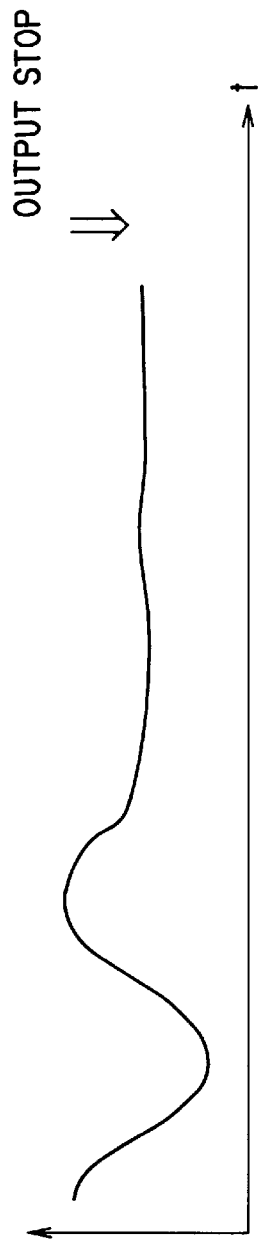
FIG. 35A
FIG. 35B
FIG. 35C
FIG. 35D
FIG. 35E

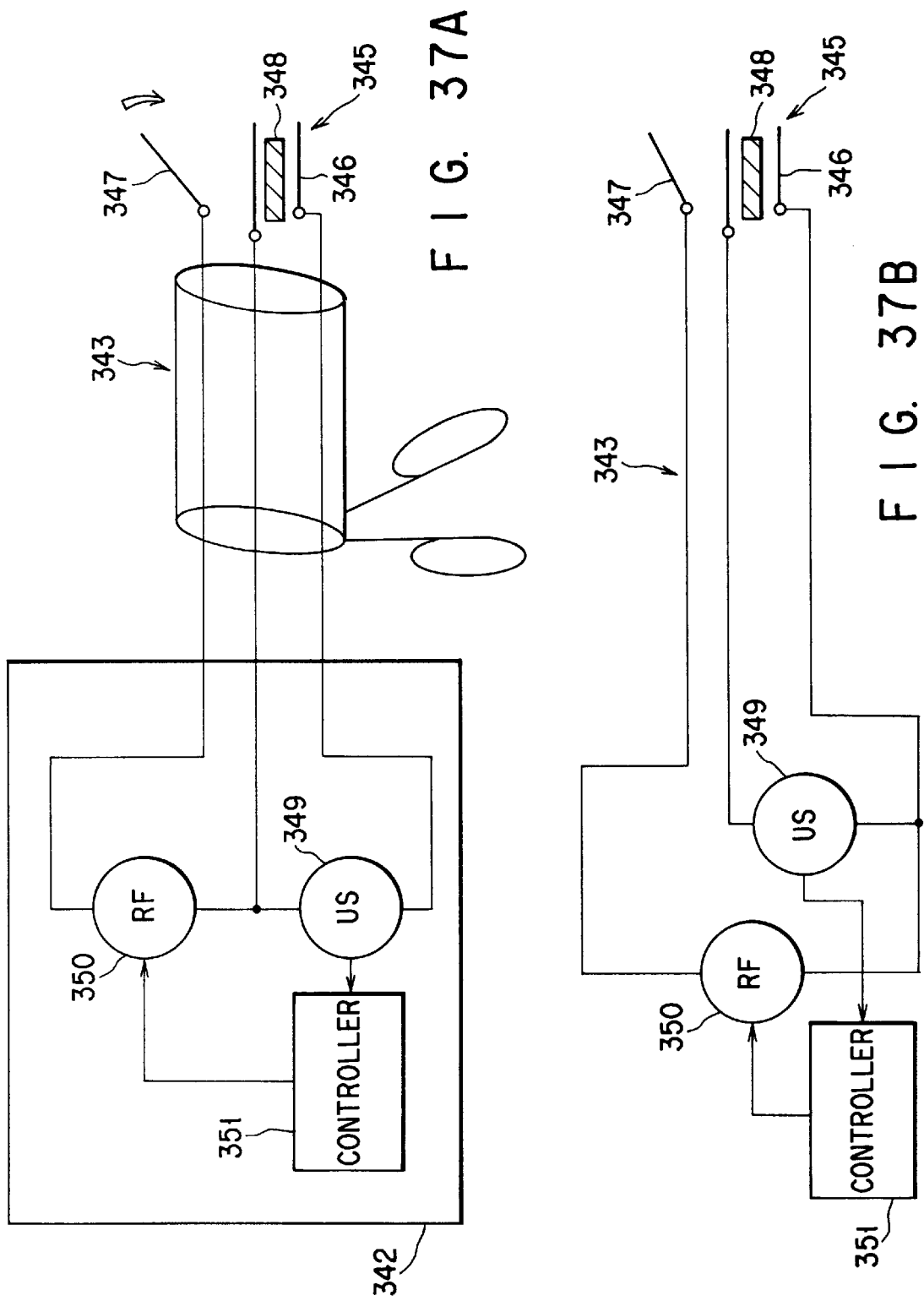

ELECTROSURGERY APPARATUS AND MEDICAL APPARATUS COMBINED WITH THE SAME

BACKGROUND OF THE INVENTION

The present invention relates to an electrosurgery apparatus for performing abscission or hemostasis of a living tissue by using a high-frequency power.

In general, an electrosurgery apparatus such as an electric scalpel is used in a surgical operation or in an internal treatment in order to cut a living tissue, coagulate a bleeding site or stop bleeding. The electrosurgery apparatus comprises a high-frequency cautery power supply unit (hereinafter referred to as "cautery power supply") and a treatment device connected to the cautery power supply. The treatment device is provided with a contact portion to be put in contact with the living tissue. A treatment electrode is mounted on the contact portion.

When the electrosurgery apparatus is used, a high-frequency power (electric energy) for treatment is supplied to the treatment electrode, with the contact portion of the treatment device being put in contact with a treatment site or a living tissue, thereby performing a medical treatment.

As regards the electrosurgery apparatus with the conventional structure, when a living tissue is to be cut, a bleeding site is to be coagulated or bleeding is to be stopped, the output level of high-frequency power output from the cautery power supply unit of the electrosurgery apparatus is set by an operator on the basis of his/her own skill or experience. In an actual electrosurgical operation for hemostasis, the degree of hemostasis or the quality of coagulation is determined by considering an output time of high-frequency power output from the cautery power supply or observing the treatment site. Under the circumstances, it is difficult to exactly control the high-frequency power output from the cautery power supply. Thus, it is difficult to cut a living tissue, coagulate a bleeding site or stop bleeding, with high efficiency with optimal high-frequency power.

In some electrosurgery apparatus, the output of high-frequency power is automatically controlled. However, since the conditions of use of electrosurgery apparatus varies depending on symptoms, the degree of cautery may vary due to differences in living tissues to be treated, portions to be cauterized, the type of the electrode, the contact pressure of the electrode on the living tissue, etc. Thus, with the conventional electrosurgery apparatus, the output of high-frequency power cannot exactly be controlled.

BRIEF SUMMARY OF THE INVENTION

The present invention has been made in consideration of the above circumstance, and its object is to provide an electrosurgery apparatus capable of exactly detecting the condition of treatment of a living tissue or a load.

In order to achieve the above object, there is provided an electrosurgery apparatus including a treatment device having treatment means for treating a living tissue, and energy supply means for supplying treatment energy to the treatment means, wherein the living tissue is treated by the treatment means while the treatment energy is being supplied to the treatment means, the apparatus comprising:

variation detection means for detecting a variation in condition of the energy supplied to the treatment means while the living tissue is being treated; and living body information detection means for acquiring living body information on the living tissue to be treated, on the basis of detection data obtained by the variation detection means.

While a living tissue is cut or coagulated for hemostasis, a variation in state of treatment energy supplied to the treatment means is detected by the living body information detection means. Living body information on the living tissue to be treated is obtained on the basis of the detected variation, and an output of the apparatus is controlled on the basis of the living body information.

There is also provided an electrosurgery apparatus including a treatment device having treatment means for treating a living tissue, and energy supply means for supplying treatment energy to the treatment means, wherein the living tissue is treated by the treatment means while the treatment energy is being supplied to the treatment means, the apparatus comprising:

examination output generating means for generating an examination output for examining the state of the living tissue;

examination output supply means for supplying the examination output, which is generated by the examination output generating means, to the treatment means; and living body information detection means for detecting a variation in the examination output and acquiring living body information on the living tissue to be treated, on the basis of the detected variation in the examination output.

There is also provided a medical apparatus in which an electrosurgery apparatus for treating a living tissue is combined with an endoscope, the electrosurgery apparatus having a treatment device with treatment means for treating the living tissue, and energy supply means for supplying treatment energy to the treatment means, the electrosurgery apparatus comprising:

variation detection means for detecting a variation in condition of the energy supplied to the treatment means while the living tissue is being treated; and living body information detection means for acquiring living body information on the living tissue to be treated, on the basis of detection data obtained by the variation detection means, and the endoscope comprising observation means capable of observing an operation of the treatment means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 schematically shows the structure of the whole system of an electrosurgery apparatus according to a first embodiment of the present invention;

FIG. 3 is a characteristic graph showing an example of a state of variation of a detected value of a voltage between an active electrode and a feedback electrode while the apparatus of the first embodiment is used;

FIG. 4 is a characteristic graph showing an example of a state of variation of a detected value of a current between the active electrode and the feedback electrode while the apparatus of the first embodiment is used;

FIG. 11 schematically shows the structure of an electrosurgery apparatus according to a second embodiment of the present invention;

FIG. 12 schematically shows the structure of an electrosurgery apparatus according to a third embodiment of the present invention;

FIG. 13 is a characteristic graph showing a variation in impedance at the time of treatment by the electrosurgery apparatus according to the third embodiment;

FIG. 14 is a flow chart illustrating the operation of the electrosurgery apparatus according to the third embodiment;

FIG. 20 schematically shows the structure of a main part of the fifth embodiment;

FIG. 21 is a characteristic graph showing a state wherein a detection output wave is superimposed on a treatment output wave in the fifth embodiment;

FIG. 22A is a characteristic graph showing variation characteristics of impedance Z of a living body in the fifth embodiment;

FIG. 22B is a characteristic graph showing variation characteristics of impedance Z of a living body in a modification of the fifth embodiment;

FIG. 23A schematically shows the structure of a main part of an electrosurgery apparatus according to a sixth embodiment of the invention;

FIG. 23B schematically shows the structure of a main part in a modification of the sixth embodiment of the invention;

FIG. 26A is a perspective view showing a connection state of an adapter of an electrosurgery apparatus according to a ninth embodiment of the invention;

FIG. 26B schematically shows the structure of an electric circuit within the adapter of the electrosurgery apparatus according to the ninth embodiment;

FIG. 31 schematically shows the structure of a main part of a 14th embodiment of the invention;

FIG. 32 is a perspective view of an electric scalpel apparatus according to a 15th embodiment of the invention;

FIG. 33A schematically shows the structure of a main part of an adder circuit in the 15th embodiment of the invention;

FIG. 33B is a characteristic graph showing a frequency-adjusted waveform;

FIG. 34A schematically shows the structure of a main part of an electric scalpel apparatus according to a 16th embodiment of the present invention;

FIG. 34B is a characteristic graph showing a first output waveform of the electric scalpel apparatus according to the 16th embodiment;

FIG. 34C is a characteristic graph showing a second output waveform of the electric scalpel apparatus according to the 16th embodiment;

FIG. 35A is a characteristic graph showing a variation in output waveform of the electric scalpel apparatus according to the 16th embodiment;

FIG. 35B is a characteristic graph of an output of the electric scalpel according to the 16th embodiment;

FIG. 35C is a characteristic graph of an R component current of the electric scalpel according to the 16th embodiment;

FIG. 35D is a characteristic graph of a C component current of the electric scalpel according to the 16th embodiment;

FIG. 35E is a characteristic graph showing a variation in C component current of the electric scalpel according to the 16th embodiment;

FIG. 37A schematically shows the structure of the electrosurgery apparatus according to the 17th embodiment;

FIG. 37B schematically shows the structure of a first modification of the 17th embodiment;

DETAILED DESCRIPTION OF THE INVENTION

Figures 2A, 2B:
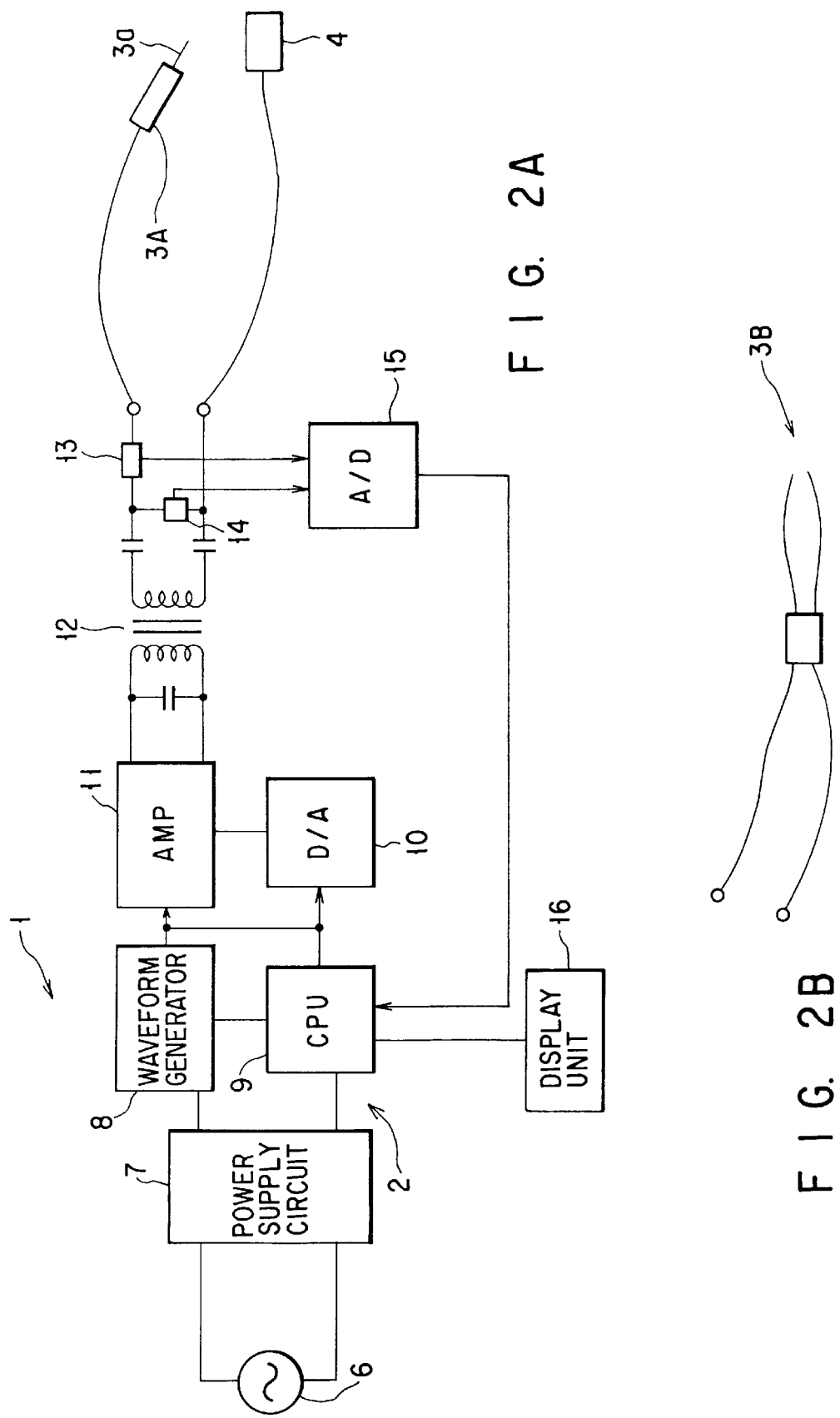
FIG. 2A schematically shows the structure of an electric circuit in a state wherein a monopolar treatment device is connected to the electrosurgery apparatus according to the first embodiment.
FIG. 2B schematically shows the structure of a bipolar treatment device connected to the electrosurgery apparatus.

A first embodiment of the present invention will now be described with reference to FIGS. 1 to 7. FIG. 1 schematically shows the structure of the whole system of an electrosurgery apparatus 1 according to the first embodiment. The electrosurgery apparatus 1 includes a high-frequency cautery power supply unit (hereinafter referred to as "cautery power supply") 2. The cautery power supply 2 is connected to a treatment device 3, a patient electrode 4 and a footswitch 5. A monopolar treatment device 3A shown in FIG. 2A and a bipolar treatment device 3B shown in FIG. 2B are examples of the treatment device 3 used in the electrosurgery apparatus 1.

The cautery power supply 2 comprises, as shown in FIG. 2A, a power supply circuit 7 which receives power from a commercial power supply 6 and generates various voltages via an insulated transformer (not shown); a waveform generator 8 which receives power from the power supply circuit 7 and generates high-frequency waveform signals corresponding to various treatments such as incision and coagulation; a control CPU (output control means) 9; A D/A converter 10 which receives a control signal from the CPU 9 and outputs high-frequency signals; a high-frequency power amplifier 11 for high-frequency amplifying the signals generated by the waveform generator 8; and an output transformer (energy supply means) 12. An output port of the output transformer 12 is connected to the monopolar treatment device 3A and patient electrode 4.

The electrosurgery apparatus 1 of the present embodiment includes an active electrode (treatment means) 3a provided on the monopolar treatment device 3A; a current sensor (living-body information sensing means) 13 for sensing a current between the patient electrode 4 and a feedback electrode; and a voltage sensor (living-body information sensing means) 14 for sensing a voltage between the patient electrode 4 and the feedback electrode. The current sensor 13 and voltage sensor 14 are connected to an A/D converter 15. The A/D converter 15 is connected to the CPU 9. Current detection data delivered from the current sensor 13 and voltage detection data from the voltage sensor 14 are input to the A/D converter 15. The A/D converter 15 converts the received analog current detection data and voltage detection data to digital data and delivers the same to the CPU 9.

The CPU 9 has a control function of controlling the output of high-frequency signals. According to this control function, a voltage variation and a current variation, or at least one of them, is detected on the basis of the signal input to the CPU 9 from the A/D converter 15. A most proper one of parameters, such as the initial value of the detected result, maximum value MAX, minimum value MIN, a rate of change, etc., is selected as a condition for finishing cautery, and the output of the high-frequency signal is controlled on the basis of the selected parameter.

The CPU 9 is connected to a display unit 16 for displaying various information relating to high-frequency treatment.

Figure 6:
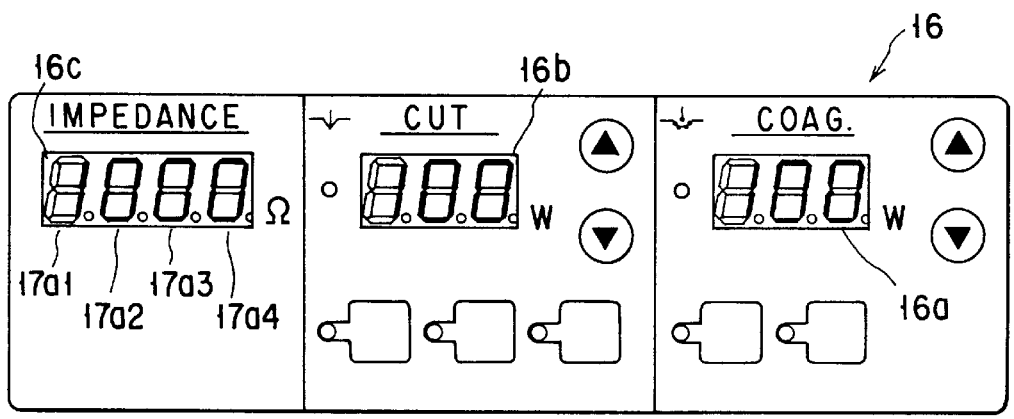
FIG. 6 is a plan view of a display unit of the apparatus according to the first embodiment.

The display unit 16 comprises, as shown in FIG. 6, a COAG display section 16a for displaying information relating to high-frequency power at the time of coagulating a living tissue, a set value of the high-frequency power, etc.; a CUT display section 16b for displaying information relating to high-frequency power at the time of cutting a living tissue, a set value of this high-frequency power, etc.; and an impedance display section 16c for displaying information relating to a living tissue to be treated.

The impedance display section 16c is provided with four-digit digital display elements 17a1 to 17a4. Each of digital display elements 17a1 to 17a4 has 7 segments for digitally displaying one of numerals 0 to 9. When high-frequency treatment is performed by the electrosurgery apparatus 1 of the present embodiment, the CPU 9 finds an impedance on the basis of the current value and voltage value detected by the current sensor 13 and voltage sensor 14 and sends the value of the found impedance to the display unit 16. The impedance display section 16c of the display unit 16 displays the value of the impedance on the four-digit digital display elements 17a1 to 17a4 directly by numerals, thereby indicating the current impedance value.

Figure 8:
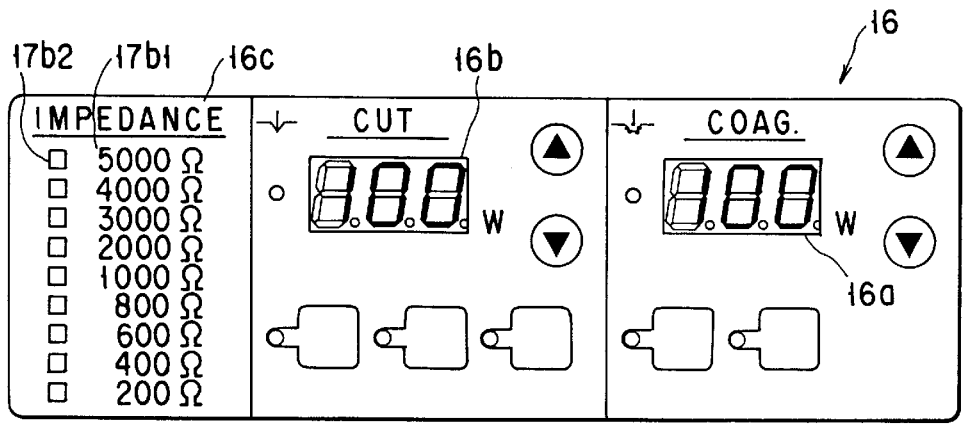
FIG. 8 is a plan view showing a first modification of the display unit of the first embodiment.
Figure 9:
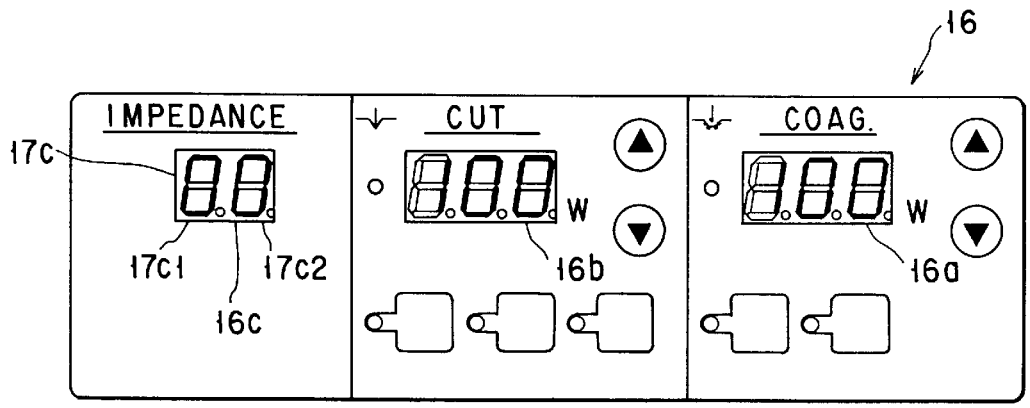
FIG. 9 is a plan view showing a second modification of the display unit of the first embodiment.
Figure 10:
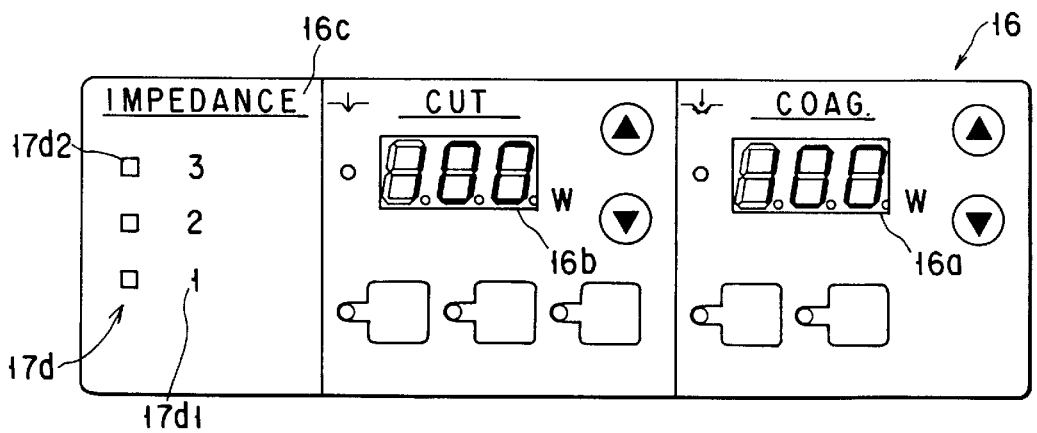
FIG. 10 is a plan view showing a third modification of the display unit of the first embodiment.

FIGS. 8 to 10 show modifications of the display unit 16 provided on the electrosurgery apparatus 1 of the first embodiment.

An impedance display section 16c according to a first modification shown in FIG. 8 comprises a bar graph display section. The impedance display section 16c includes vertically arranged impedance gradations 17b1 indicating numerical values of impedance, and rectangular LEDs 17b2 arranged on the side of the numerical values of impedance gradations 17b1. In this modification, when high-frequency treatment is performed, if the impedance value obtained by the CPU 9 is greater than the numerical value of any of the impedance gradations 17b1 on the impedance display section 16c, the rectangular LED 17b2 on the side of the associated impedance gradation 17b1 is turned on. Thus, the current impedance value is indicated.

The impedance display sections 16c of display units 16 shown in FIGS. 6 and 8 display absolute values of impedance. By contrast, a level display section 17c and a level display section 17d according to second and third modifications shown in FIGS. 9 and 10 display the level of impedance value.

The level display section 17c of the second modification shown in FIG. 9 comprises two-digit digital display elements 17c1 and 17c2. The digital display elements 17c1 and 17c2 digitally display two of numerals 0 to 9 by means of two sets of 7 segments. In this modification, the digital display elements 17c1 and 17c2 numerically display the level of impedance. For example, when level 1 is displayed, it indicates about 200 Ω. The impedance value assigned to the displayed level may be predetermined by the manufacturer or user.

The level display section 17d according to the third modification shown in FIG. 10 comprises vertically arranged level gradations 17d1 indicating numerical levels of impedance, and rectangular LEDs 17d2 arranged on the side of associated numeral levels of impedance gradations 17d1. In this modification, when high-frequency treatment is performed, the rectangular LED 17b2 on the side of the numerical value of level gradation 17d1 associated with the impedance value obtained by the CPU 9 is turned on. Thus, the level of current impedance value is indicated.

There are other display methods. For example, if the impedance value is within a range predetermined by the manufacturer, it may be displayed by 7-segment digital display elements 17a1 to 17a4 shown in FIG. 6 or 17c1 and 17c2 shown in FIG. 9, or it may be indicated by green light of the LEDs 17b2 shown in FIG. 8 or LEDs 17d2 shown in FIG. 10. If the impedance value exceeds the predetermined range, it may be indicated by red light of the LEDs. Alternatively, if the impedance value is within the predetermined range, it may be displayed by 7-segment digital display elements 17a1 to 17a4 shown in FIG. 6 or 17c1 and 17c2 shown in FIG. 9, or it may be indicated by turning-on of the LEDs 17b2 shown in FIG. 8 or LEDs 17d2 shown in FIG. 10. If the impedance value exceeds the predetermined range, it may be indicated by flickering of light.

The operation of the above structure will now be described. For example, when a bleeding site of a living tissue is coagulated or bleeding is stopped by using the electrosurgery apparatus 1 of the present embodiment, high-frequency power is supplied to the active electrode 3a of monopolar treatment device 3A from the cautery power supply 2. At the time of this medical treatment, the supply of high-frequency power is started, as shown in FIGS. 3 and 4. The detected voltage data from the voltage sensor 14 varies, as shown in FIG. 3, and the detected current data from the current sensor 13 varies, as shown in FIG. 4, from the time instant T0 of start of coagulation treatment of the living tissue, as the coagulation (carbonization) of the living tissue progresses.

Specifically, the detected voltage data from the voltage sensor 14 gradually increases, with the passing of time, from the treatment start time T0. When coagulation (carbonization) of the living tissue becomes close to the end, the rate of increase of voltage gradually decreases. The detected current data from the current sensor 13 gradually decreases, with the passing of time, from the treatment start time T0. When coagulation (carbonization) of the living tissue becomes close to the end, the rate of decrease of current gradually decreases.

At the time of treatment of the living tissue, the CPU 9, detects, on the basis of the input signal from the A/D converter 15, a voltage variation rate ($\Delta V/\Delta T$) and a current variation rate ($\Delta I/\Delta T$).

At this time, $$\Delta V = \Delta y = y(T2) - y(T1)$$

The voltage variation rate $\Delta V/\Delta T$ is given by $$\Delta V/\Delta T = y(T2) - y(T1)/T2 - T1$$

The CPU 9 outputs a control signal to stop cautery or automatically decrease an output, when it is detected that the voltage variation rate ($\Delta V/\Delta T$) has decreased to a predetermined value or below, when it is detected that the detected voltage data has fallen out of the range between yMAX and yMIN, or when it is detected that the value y|N| has fallen out of the range between yMAX and yMIN.

In addition, the CPU 9 outputs a control signal to stop cautery or automatically decrease an output, when it is detected that the current variation rate ($\Delta I/\Delta T$) has decreased to a predetermined value or below, when it is detected that the detected current data has fallen out of the range between yMAX and yMIN, or when it is detected that the value y|N| has fallen out of the range between yMAX and yMIN.

Figure 7:
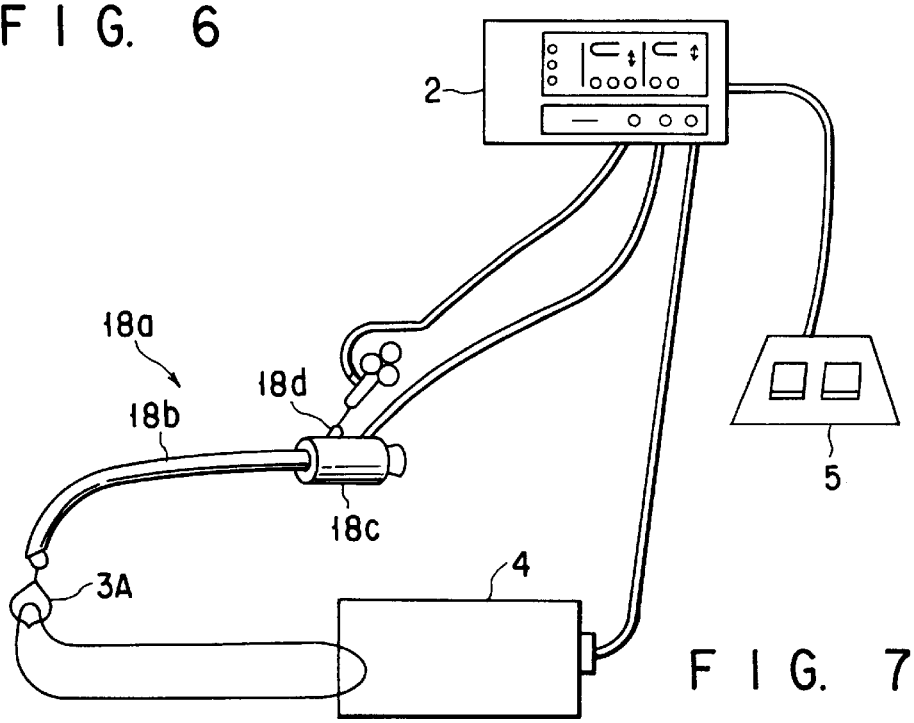
FIG. 7 schematically shows the structure of an endoscope system combined with the monopolar treatment device of the apparatus of the first embodiment.

The monopolar treatment device 3A of this embodiment may be combined with an endoscope 18a, as shown in FIG. 7. The endoscope 18a comprises an insertion portion 18b to be inserted into the body of a patient and a proximal-end operation unit 18c coupled to a proximal end of the insertion portion 18b.

The operation unit 18c is provided with an inlet portion for a treatment device insertion channel 18d. An outlet portion of the insertion channel 18d is situated at a distal end portion of the insertion portion 18. The monopolar treatment device 3A is inserted from the inlet portion of the insertion channel 18d, passed through the insertion channel 18d, drawn out of the outlet portion of the insertion channel 18d, and guided into a living tissue to be treated.

The apparatus with the above structure has the following advantage. In this embodiment, when a bleeding site of a living body is coagulated or bleeding is stopped, the voltage variation rate ($\Delta V/\Delta T$) and current variation rate ($\Delta I/\Delta T$) are detected on the basis of detection signals from the current sensor 13 and voltage sensor 14. Thus, information on the living tissue to be treatment is obtained. In addition, a most proper one of parameters, such as the initial value of the detected result, maximum value MAX, minimum value MIN, a rate of change, etc., is selected by the CPU 9 as a condition for finishing cautery, and the output of the high-frequency signal is controlled on the basis of the selected parameter. Therefore, the high-frequency power output can be controlled with high precision, and stable coagulation performance and hemostasis performance can be achieved. As a result, cautery with predetermined quality can be performed in accordance with varying conditions for treatment such as the active electrode 3a of monopolar treatment device 3A, the living body, etc.

Excessive carbonization of a living body or a short-circuit of the electrode of the monopolar treatment device 3A can be detected. Thus, useless output from the active electrode 3a of monopolar treatment device 3A can be prevented.

Figure 5:
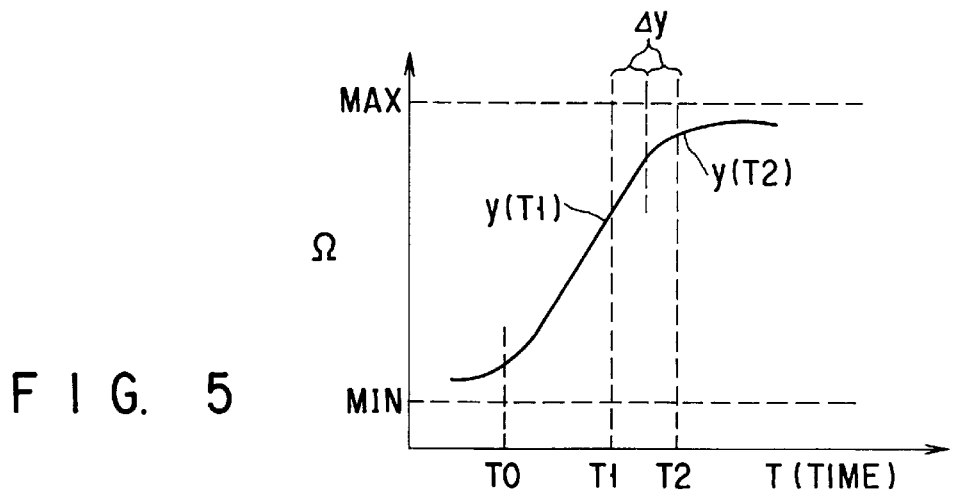
FIG. 5 is a characteristic graph showing an example of a state of variation of a detected value of an impedance between the active electrode and the feedback electrode while the apparatus of the first embodiment is used.

The following technique may be adopted. An impedance between the active electrode 3a of monopolar treatment device 3A and a feedback electrode of the patient electrode 4 is detected on the basis of the detected current data from the current sensor 13 and the detected voltage data from the voltage sensor 14. As is shown in FIG. 5, the variation characteristics of the impedance is detected. The initial impedance, the variation rate of impedance, the upper limit of impedance and the lower limit of impedance are detected. A most proper one of these parameters is selected as a condition for completing cautery and the output power is automatically or semi-automatically controlled.

The cautery power supply 2 of electrosurgery apparatus 1 may be provided with a change-over switch for selecting one of an automatic control mode and a manual mode for controlling high-frequency output. Thereby, the automatic control mode and the manual mode for controlling high-frequency output may be switched.

The display unit 16 of this embodiment is applicable not only to the electrosurgery apparatus 1 of this embodiment but also to electrosurgery apparatus 1 of other embodiments.

FIG. 11 shows a second embodiment of the present invention. An electric scalpel apparatus 41 according to the second embodiment of the invention comprises a high-frequency power generator 42, an output transformer 43, an impedance detector 44, an impedance detection signal processor 45, and a main controller 46.

The impedance detector 44 detects an impedance of a living tissue placed between a pair of electrodes of a bipolar treatment device 47 connected to an output port of the output transformer 43. The impedance detection signal processor 45 processes the signal obtained by the impedance detector 44. The main controller 46 controls the entire electric scalpel apparatus 41. The main controller 46 automatically controls turning on/off of high-frequency power on the basis of the signal output from the impedance detection signal processor 45.

The operation of the above structure will now be described. When treatment such as coagulation or hemostasis is performed on the living tissue by using the electric scalpel apparatus 41 of this embodiment, the impedance |z| of the living tissue between the electrodes of the bipolar treatment device 47 is detected by the impedance detector 44. The potential at point (a) of the impedance detector 44 varies in accordance with the detected impedance value of |z|. The potential at point (a) is compared with a reference value (Vref), thereby to automatically control start/stop of high-frequency power.

According to the above structure, (1) when load |z| is low, for example, before the start of cautery, the output signal from the impedance detection signal processor 45 is at "H" level, and the supply of power is started, and (2) when load |z| is high, for example, after the start of cautery, the output signal from the impedance detection signal processor 45 is at "L" level, and the supply of power is stopped.

The potential at point (a) may be directly converted to a digital signal in order to control high-frequency power supply.

In the above structure, the start/stop of high-frequency power supply can be automatically controlled while monitoring the state of the load |z|. Therefore, stable and sure treatment can be performed, without the need to visually observe the treatment site. In the case where a small cautery site is treated in a bipolar mode by means of the electric scalpel apparatus, even if the visual observation of the small cautery site is affected by the treatment device, etc., there is no possibility of excessive cautery of the treatment site.

FIGS. 12 to 14 show a third embodiment of the present invention. FIG. 12 schematically shows the entire structure of the system of an electrosurgery apparatus 91 according to the third embodiment. The electrosurgery apparatus 91 is provided with a cautery power supply 92. Output connectors 92a and 92b of the cautery power supply 92 are connected to a monopolar treatment device 93 and a patient electrode 94.

The cautery power supply 92 comprises a power supply circuit 95 for receiving power from a commercial power supply (not shown) and generating various voltages via an insulating transformer (not shown); a waveform generator 96 for generating high-frequency waveform signals to be used for various treatments such as cutting or coagulation, on the basis of power generated by the power supply circuit 95; a controller 97; and an output transformer 98. An output port of the output transformer 98 is connected to the monopolar treatment device 93 and patient electrode 94 via output connectors 92a and 92b, respectively.

The electrosurgery apparatus 91 of this embodiment includes an active electrode (treatment electrode) 93a provided on the monopolar treatment device 93; a current detector 99 for detecting a current between the active electrode 93a and a feedback electrode of the patient electrode 94; and a voltage detector 100 for detecting a voltage between the active electrode 93a and feedback electrode of the patient electrode 94. The voltage detector 100 is formed of windings for measuring a voltage, which are provided on the primary winding side of the output transformer 98.

The current detector 99 and voltage detector 100 are connected to an impedance detector 101. The impedance detector 101 is connected to the controller 97. The impedance detector 101 receives current detection data from the current detector 99 and voltage detection data from the voltage detector 100, thereby detecting an impedance of a living tissue placed between the active electrode 93a of monopolar treatment device 93 and the feedback electrode of patient electrode 94.

An impedance detection signal from the impedance detector 101 is input to the controller 97. The controller 97 has control functions of controlling the power supply circuit 95 and waveform generator 96 on the basis of the impedance detection signal input from the impedance detector 101, and stopping the supply of high-frequency signals when a variation range of impedance exceeds a predetermined value. The controller 97 may be constructed so as to lower the output of high-frequency signals when a variation range of impedance exceeds a predetermined value.

The operation of the above structure will now be described. When treatment such as coagulation or hemostasis is performed on the living tissue by using the electrosurgery apparatus 92 of this embodiment, high-frequency power is supplied from the cautery power supply 92 to the active electrode 93a of monopolar treatment device 93. Thus, high-frequency cautery treatment such as coagulation or hemostasis for the living tissue is performed.

FIG. 13 shows a general variation of impedance in the living tissue at the time of high-frequency cautery treatment. The impedance in the living tissue is kept constant in a normal state from a treatment start time T0, at which supply of high-frequency power is started, to a time T1 at which protein denaturing (coagulation) of the living tissue begins. From the time T1 at which protein denaturing of the living tissue begins, the impedance in the living tissue gradually increases. If the protein denaturing further progresses, carbonization of the living tissue begins. After a carbonation beginning time T2, the impedance in the living tissue varies extremely. That is, the impedance increases and decreases alternately.

In the electrosurgery apparatus 91 of this embodiment, the operation illustrated in FIG. 14 is carried out at the time of high-frequency cautery treatment. Specifically, in step S1, a minimum value Zmin of impedance in the living tissue after the beginning of the high-frequency cautery treatment is set and the number of measuring operations, n, is set at zero.

In step S2, the measurement value Z of impedance is detected. In step S3, the number of measuring operations, n, is counted as one. In step S4, the measurement value Z of impedance detected in step S2 is compared with the minimum value Zmin of impedance. If Z<Zmin, the measurement value Z of impedance detected in step S2 is set at Zmin in subsequent step S5.

In cases other than Z<Zmin or if the value Z is set at Zmin in step S5, it is determined in step S6 whether the number of impedance measuring operations, n, is ten or above. If $n \geq 10$, the operations of steps S2 to S6 are repeated.

If $n \geq 10$ in step S6, the impedance measurement value Z is detected in subsequent step S7. In step S8, the impedance measurement value Z detected in step S7 is compared with the impedance minimum value Zmin. If Z<Zmin, the impedance measurement value Z detected in step S7 is set at Zmin in subsequent step S9.

In cases other than Z<Zmin or if the impedance measurement value Z detected in step S7 is set at Zmin in step S9, the function f (Zmin) of the impedance minimum value is calculated in step S10. Thereby, a reference value ΔZref of impedance variation width ΔZ is set.

In step S11, a maximum value Zmax (10) of impedance value Z in the last 10 detection operations is selected. In step S12, a minimum value Zmax (10) of impedance value Z in the last 10 detection operations is selected.

In step S13, a variation range ΔZ of impedance measurement value Z in the last 10 detection operations is calculated from Zmax (10)–Zmin (10). In step S14, ΔZ and ΔZref are compared. In cases other than ΔZ>ΔZref, the operations of steps S7 to S14 are repeated.

If ΔZ>ΔZref in step S14, the supply of high-frequency power is stopped. In this case, instead of stopping the supply of high-frequency power, the output of high-frequency power may be decreased.

The above-described structure can bring about the following advantages. In the electrosurgery apparatus 91 of this embodiment, when treatment such as coagulation or hemostasis for the living tissue is performed, the current detection data from the current detector 99 and the voltage detection data from the voltage detector 100 are delivered to the impedance detector 101. The impedance detector 101 thus detects an impedance in the living tissue placed between the active electrode 93a of monopolar treatment device 93 and the feedback electrode of patient electrode 94. On the basis of the impedance detection signal output from the impedance detector 101, the controller 97 controls the power supply circuit 95 and waveform generator 96. If the variation range ΔZ of impedance exceeds hm value ΔZref, the controller 97 stops the output of high-frequency signals. Therefore, the output of high-frequency power can be controlled with high precision, and carbonization of the living tissue at the time of high-frequency cautery treatment can be limited to a minimum.

In the present embodiment, the voltage detector 100 is formed of windings for measuring a voltage, which are provided on the primary winding side of the output transformer 98. Thus, there is no need to provide voltage measurement means in the patient-side circuit including the monopolar treatment device 93 and the feedback electrode of patient electrode 94. Therefore, the entire structure of the electrosurgery apparatus 91 can be simplified.

In this embodiment, the impedance detector 101 detects the impedance in the living tissue and if the variation range ΔZ of impedance exceeds the predetermined value ΔZref, the controller 97 stops the output of high-frequency signals. However, the output of high-frequency signals may be similarly controlled on the basis of either the current detection data from the current detector 99 or the voltage detection data from the voltage detector 100.

Figure 15:
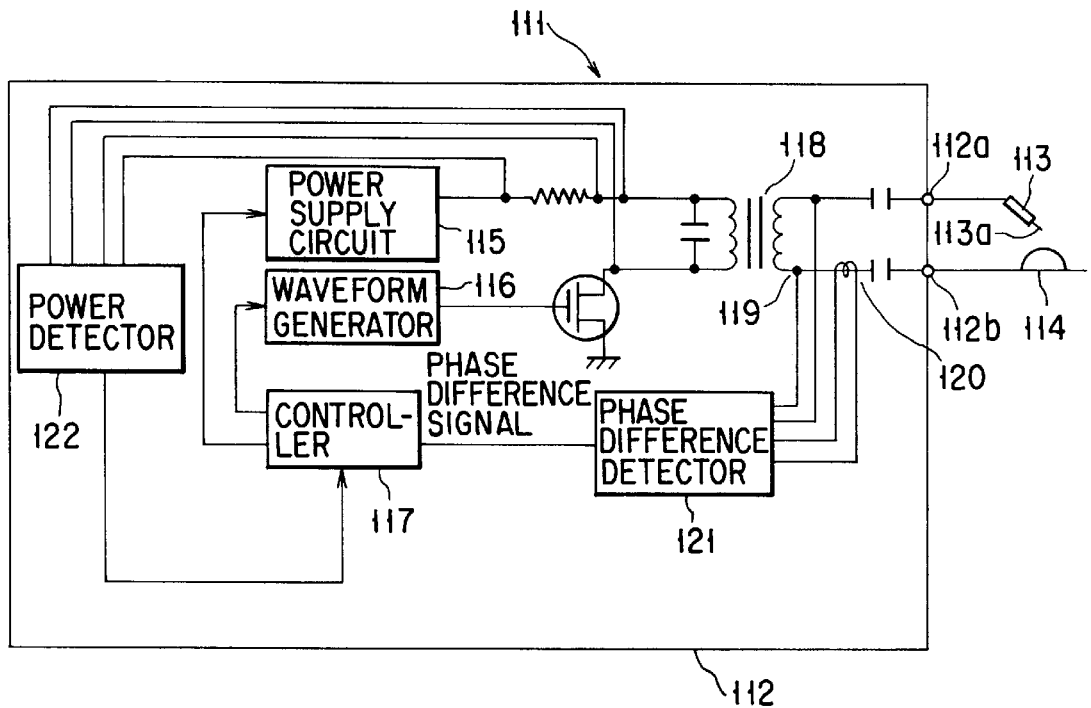
FIG. 15 schematically shows the structure of an electrosurgery apparatus according to a fourth embodiment of the invention.

FIGS. 15 to 18 show a fourth embodiment of the invention. FIG. 15 schematically shows the entire structure of the system of an electrosurgery apparatus 111 according to the fourth embodiment. The electrosurgery apparatus 111 is provided with a cautery power supply 112. Output connectors 112a and 112b of the cautery power supply 112 are connected to a monopolar treatment device 113 and a patient electrode 114.

The cautery power supply 112 comprises a power supply circuit 115 for receiving power from a commercial power supply (not shown) and generating various voltages via an insulating transformer (not shown); a waveform generator 116 for generating high-frequency waveform signals to be used for various treatments such as cutting or coagulation, on the basis of power generated by the power supply circuit 115; a controller 117; and an output transformer 118. An output port of the output transformer 118 is connected to the monopolar treatment device 113 and patient electrode 114 via output connectors 112a and 112b, respectively.

The electrosurgery apparatus 111 of this embodiment includes an active electrode (treatment electrode) 113a provided on the monopolar treatment device 113 on the secondary winding side of the output transformer 118; a voltage detector 119 for detecting a voltage between the active electrode 113a and a feedback electrode of the patient electrode 114; and a current detector 120 for detecting a current between the active electrode 113a and feedback electrode of the patient electrode 114.

The voltage detector 119 and current detector 120 are connected to a phase difference detector 121. The phase difference detector 121 receives voltage detection data from the voltage detector 119 and current detection data from the current detector 120, thereby detecting a phase difference in output voltage and output current.

A phase difference detection signal output from the phase difference detector 121 is input to the controller 117. The controller 117 has control functions of controlling the power supply circuit 115 and waveform generator 116 on the basis of the phase difference detection signal input from the phase difference detector 121, and stopping the supply of high-frequency signals when a value of phase difference falls out of a predetermined range, when the rate of variation of phase difference exceeds a predetermined value, or when a variation range of phase difference exceeds a predetermined value. The controller 117 may be constructed so as to lower the output of high-frequency signals when a value of phase difference falls out of a predetermined range, when the rate of variation of phase difference exceeds a predetermined value, or when a variation range of phase difference exceeds a predetermined value.

Besides, the electrosurgery apparatus 111 of this embodiment includes a power detector 122 for measuring a voltage, a current and a power supplied to the primary winding side of the output transformer 118. The power detector 122 is connected to the controller 117. The controller 117 has control functions of increasing a voltage of the power supply circuit 115 or varying high-frequency waveform signals from the waveform generator 116, when the power detected by the power detector 122 is lower than a predetermined value.

The operation of the above-described structure will now be described. When treatment such as coagulation or hemostasis is performed on the living tissue by using the electrosurgery apparatus 111 of this embodiment, high-frequency power is supplied from the cautery power supply 112 to the active electrode 113a of monopolar treatment device 113. Thus, high-frequency cautery treatment such as coagulation or hemostasis for the living tissue is performed.

Figure 16:
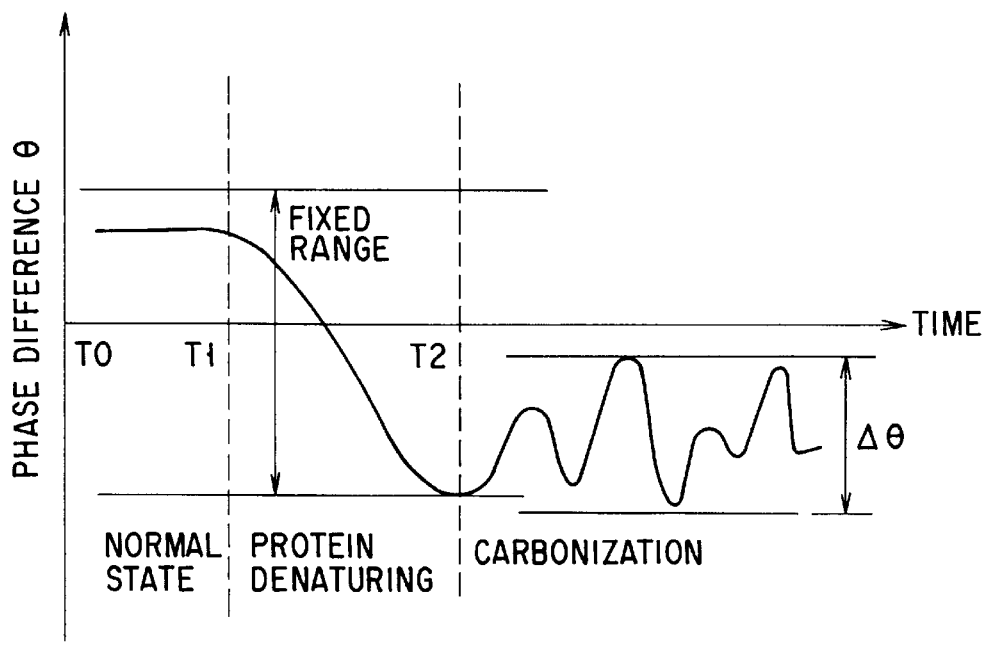
FIG. 16 is a characteristic graph showing a variation in phase difference of voltage and current at the time of high-frequency cautery by means of the electrosurgery apparatus of the fourth embodiment.

FIG. 16 shows a general variation of a phase difference in output voltage and output current at the time of high-frequency cautery treatment. The phase difference in output voltage and output current is kept constant in a normal state from a treatment start time T0, at which supply of high-frequency power is started, to a time T1 at which protein denaturing (coagulation) of the living tissue begins.

From the time T1 at which protein denaturing of the living tissue begins, the phase difference in output voltage and output current varies gradually. If the protein denaturing further progresses, carbonization of the living tissue begins. After a carbonation beginning time T2, the phase difference in output voltage and output current varies extremely. That is, the phase difference increases and decreases alternately.

Figure 17:
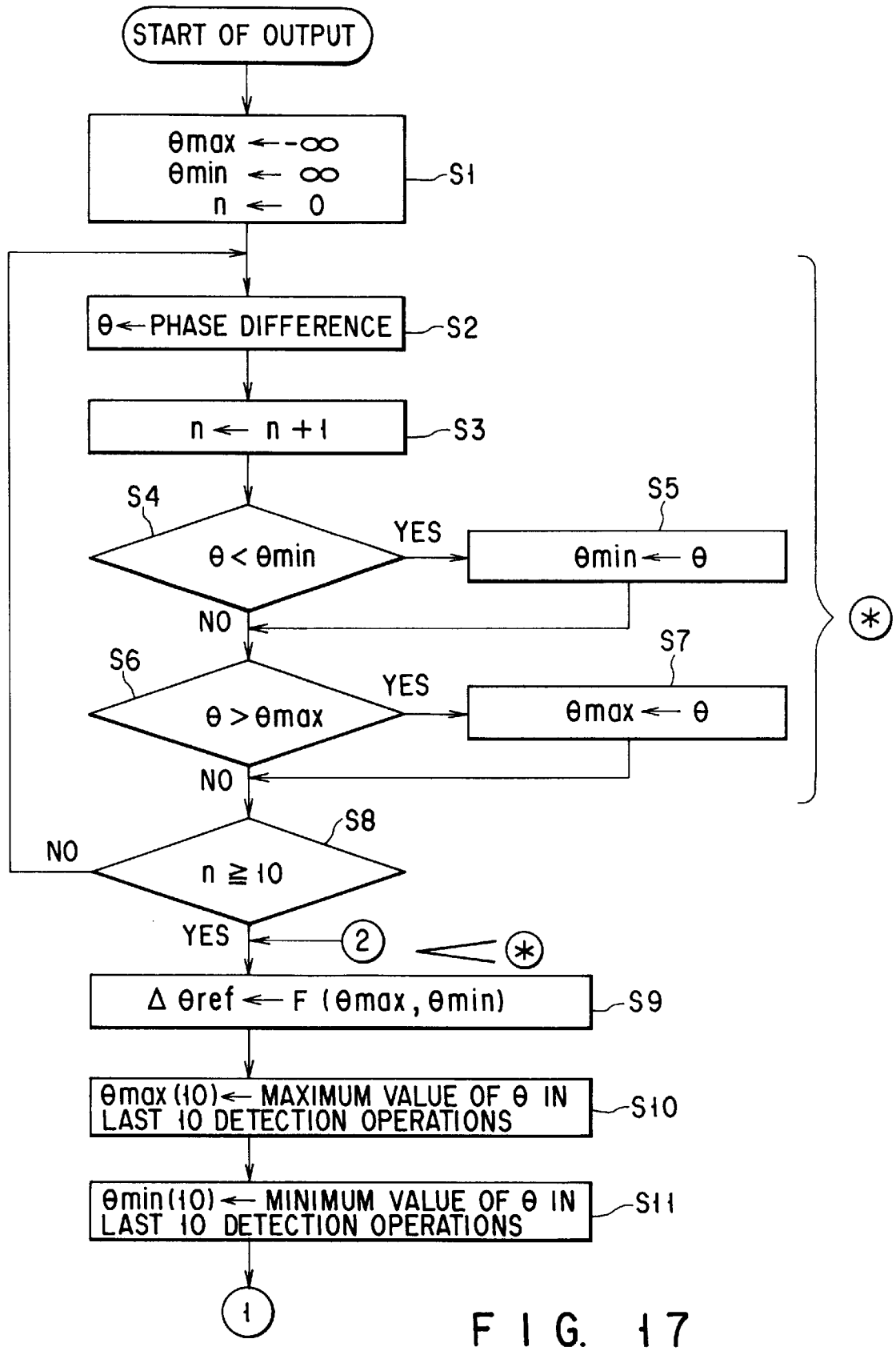
FIG. 17 is a flow chart illustrating the operation of the electrosurgery apparatus according to the fourth embodiment.
Figure 18:
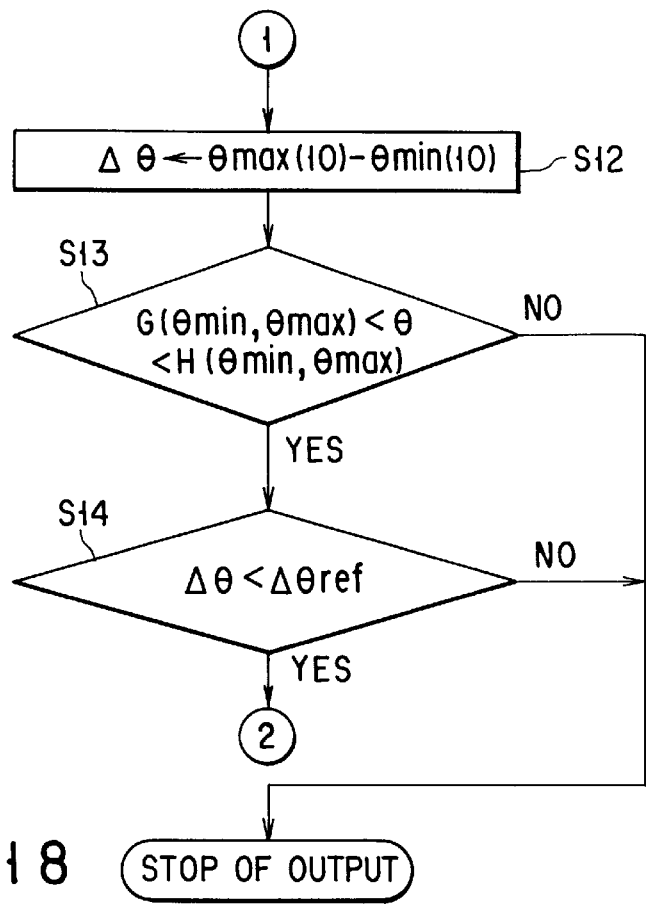
FIG. 18 is a flow chart illustrating the operation of the electrosurgery apparatus according to the fourth embodiment.

In the electrosurgery apparatus 111 of this embodiment, the operation illustrated in FIGS. 17 and 18 are carried out at the time of high-frequency cautery treatment. Specifically, in step S1, a maximum value θmax and a minimum value θmin of phase difference in output voltage and output current after the beginning of the high-frequency cautery treatment are set and the number of measuring operations, n, is set at zero.

In step S2, a measurement value θ of phase difference is detected. Subsequently, in step S3, the number of measuring operations of phase difference, n, is set at 1. In step S4, the phase difference measurement value θ obtained in step S2 is compared with the minimum value θmin. If θ<θmin, the phase difference measurement value θ obtained in step S2 is set at θmin in subsequent step S5.

In cases other than θ<θmin or if the value of θ is set at θmin in step S5, the phase difference measurement value θ obtained in step S2 is compared with the maximum value θmax in subsequent step S6. If θ>θmax, the phase difference measurement value θ obtained in step S2 is set at θmax in step S7.

In cases other than θ>θmax or if the value of θ is set at θmax in step S7, it is determined in subsequent step S8 whether the number of phase difference measuring operations, n, is ten or above. Unless n≧10, the operations of steps S2 to S8 are repeated.

If n≧10 in step S8, the second operation of steps S2 to S8 is performed. If n≧10 in step s8 of the second operation, the function F(θmax, θmin) of the maximum value θmax and minimum value θmin of phase difference is calculated, and a reference value Δθref of phase difference variation range Δθ, shown in FIG. 16, is set.

In addition, in step S10, a maximum value θmax (10) of phase difference measurement value θ in the last 10 detection operations is selected. In step S11, a minimum value θmin (10) of phase difference measurement value θ in the last 10 detection operations is selected.

In subsequent step S12, the phase difference variation range Δθ of phase difference measurement value θ in the last 10 detection operations is calculated from θmax (10)−θmin (10). Then, in step S13, it is determined whether the phase difference measurement value θ is between a maximum value H (θmin, θmax) and a minimum value G(θmin, θmax) of a predetermined set range R. If it is determined that the phase difference measurement value θ falls out of the predetermined range R, the supply of high-frequency power is stopped. In this case, instead of stopping the supply of high-frequency power, the output of high-frequency power may be decreased.

If G(θmin, θmax)<θ<H(θmin, θmax) in step S13, the next step S14 is performed. In step S14, Δθ is compared with Δθref. If Δθ<Δθref, that is, if the phase difference variation range Δθ is smaller than the reference value Δθref, the second operation of steps S2 to S8 is performed, and then steps S9 to S14 are repeated.

In step S14, in cases other than Δθ<Δθref, that is, if the phase difference variation range Δθ is greater than the reference value Δθref, the supply of high-frequency power is stopped. In this case, instead of stopping the supply of high-frequency power, the output of high-frequency power may be decreased.

The above-described structure can bring about the following advantages. In the electrosurgery apparatus 111 of this embodiment, when treatment such as coagulation or hemostasis for the living tissue is performed, the voltage detection data from the voltage detector 119 and the current detection data from the current detector 120 are delivered to the phase difference detector 121. The phase difference detector 121 thus detects a phase difference in output voltage and output current. On the basis of the phase difference detection signal output from the phase difference detector 121, the controller 117 controls the power supply circuit 115 and waveform generator 116. The supply of high-frequency signals is stopped when a value of phase difference falls out of a predetermined range, when the rate of variation of phase difference exceeds a predetermined value, or when a variation range of phase difference exceeds a predetermined value. Therefore, the output of high-frequency power can be controlled with high precision, and carbonization of the living tissue at the time of high-frequency cautery treatment can be limited to a minimum.

The electrosurgery apparatus 111 of this embodiment includes the power detector 122 for measuring a voltage, a current and a power supplied to the primary winding side of the output transformer 118. The controller 117 has functions of increasing the voltage of the power supply circuit 115 or varying high-frequency waveform signals output from the waveform generator 116, when the power detected by the power detector 122 is lower than a predetermined value. Thus, there is no need to provide signal transmission means for transmitting measurement signals between the patient circuit and the secondary circuit of the output transformer 118, which signal transmission means is required in the case where the patient circuit is provided with means for measuring a voltage, a current and a power. As compared to the case where the patient circuit is provided with means for measuring a voltage, a current and a power, the structure of the entire apparatus can be simplified.

Figure 19:
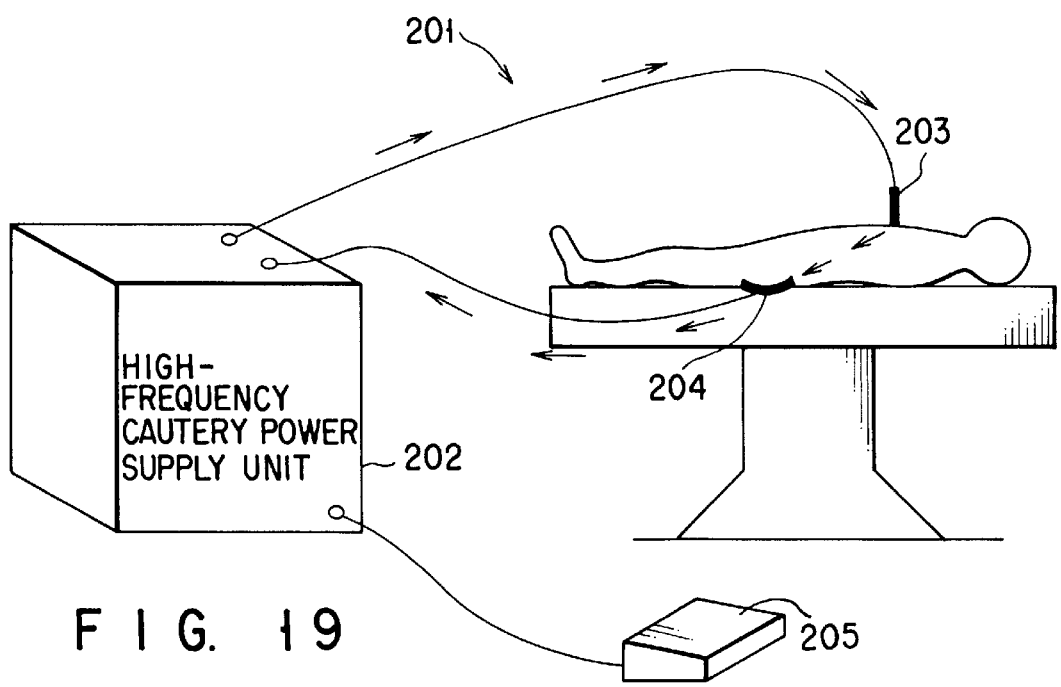
FIG. 19 schematically shows the structure of the whole system of an electrosurgery apparatus according to a fifth embodiment of the present invention.

FIGS. 19 to 22A show a fifth embodiment of the present invention. FIG. 19 schematically shows the entire structure of the system of an electrosurgery apparatus according to the fifth embodiment. The electrosurgery apparatus 201 is provided with a high-frequency cautery power supply (hereinafter referred to as "cautery power supply") 202. The cautery power supply 202 is connected to a monopolar treatment device 203, a patient electrode 204 and a footswitch 205. The monopolar treatment device 203 or a bipolar treatment device may be used as treatment device in the electrosurgery apparatus 21 of this embodiment. Both the monopolar treatment device and bipolar treatment device may be used in the electrosurgery apparatus 201.

The cautery power supply 202 comprises, as shown in FIG. 20, a treatment frequency oscillator (energy supply means) 206 and a detection frequency oscillator (examination output generating means) 207. The treatment frequency oscillator 206 generates a frequency of treatment electric energy to be supplied to a treatment electrode of the monopolar treatment device 203, for example, a high-frequency power of about several-hundred KHz. The detection frequency oscillator 207 generates a frequency different from the frequency of the treatment high-frequency output, for example, an examination signal of about several MHz for examining the condition of a living tissue.

An output terminal of the treatment frequency oscillator 206 is connected to one input terminal of an output synthesizer (examination output supply means) 210 via a preamplifier 208 and a power amplifier 209, successively. An output terminal of the detection frequency oscillator 207 is connected to the other input terminal of the output synthesizer 210 via an amplifier 211. An output terminal of the output synthesizer 210 is connected to a positive (+) side output terminal. The method of output synthesis by the output synthesizer 210 is not limited. For example, the supplied outputs may be synthesized by using a transformer or an adder comprising an amplifier, or may be simply combined by electrical connection.

The output terminal of the detection frequency oscillator 207 is also connected to a voltage detector 212. A detection signal from the voltage detector 212 is input to a tissue condition detector (living body information detection means) 213. The tissue condition detector 213 may measure only a resistance value, or may measure a dielectric constant by using phase information. In this embodiment, the method of detection by the tissue condition detector 213 is not limited.

The tissue condition detector 213 is connected to a controller 214 and also to a current detector 216 via a filter 215. The current detector 216 is connected to a negative (−) side output terminal.

The controller 214 is connected to the power amplifier 209 as well as to a display unit 217. The voltage detector 212 need not be provided if an output voltage is recognized by other means in the circuit configuration (e.g. a constant output voltage is generated, or an output voltage is limited by an instruction from the controller). The current detector 216 may comprise a current sensor, a shunt resistor, etc. as detection means. The current detector 216 may be connected not to the negative (−) side output terminal but to the positive (+) side output terminal.

It is advantageous in cost-performance and technical aspect to use a high-output circuit capable of generating a high-frequency treatment output of 1 MHz or less. However, if the output frequency is too low, the living body is adversely affected. Thus, 100 to 1000 kHz is desirable.

The detection frequency has &B dispersion at several MHz, and an impedance in the cell membrane decreases at high frequencies. Thus, information relating to the internal and external of the cell is included in the impedance information at several MHz or more. However, if the frequency is too high, a transmission loss in the cable increases, an influence of noise increases, or a circuit configuration becomes complex. Thus, about 2 to 20 MHz is desirable.

The type of filter 215 is not limited, if it can cut the treatment frequency and pass the detection frequency. In the present embodiment, the detection frequency is higher than the treatment frequency, a high-pass filter or a band-pass filter can be used.

The controller 214 of this embodiment performs the following control operations. When coagulation, cutting or adhesion is performed by treatment energy, it is determined by the tissue condition detector 213 whether such treatment is completed. Thereby, excess energy is not supplied, and stable and safe treatment is achieved. For example, the tissue condition detector 213 detects whether coagulation is completed, and the controller 214 controls the display of parameters relating to the coagulation, the display of completion of treatment, and the decrease/stop of output. A complicated control can also be performed such that the output is gradually decreased before the completion of treatment in order to prevent excessive coagulation.

The operation of the electrosurgery apparatus 201 having the above structure will now be described. When treatment such as cutting or hemostasis for a living tissue is performed, the detection frequency oscillator 207 generates an examination signal for examining the condition of the living tissue. This examination signal has a frequency different from the treatment frequency generated by the treatment frequency oscillator 206 and supplied to the treatment electrode of the monopolar treatment device 203.

As is shown in FIG. 21, the examination signal supplied from the detection frequency oscillator 207 is superimposed on the treatment frequency generated by the treatment frequency oscillator 206 by means of the output synthesizer 210. In this state, the examination signal is supplied to the treatment electrode of the monopolar treatment device 203. In addition, a variation in the examination signal is detected by the tissue condition detector 213, and on the basis of the detected data, living body information on the living tissue to be treated is obtained.

The present embodiment having the above structure can bring about the following advantages. The detection frequency generator 207 generates the examination signal for the load tissue condition, which has a frequency different from the treatment frequency generated by the treatment frequency oscillator 206. The treatment frequency differs from the detection frequency. Thus, the amount of noise contained in data can be reduced more easily by separating the detection frequency, than in the case where signals with the same frequency are used.

A frequency suitable for treatment (e.g. a frequency with which a high output can be obtained at a relatively low cost) can be chosen for the treatment high-frequency output. A frequency suitable for detection (e.g. a frequency with which the impedance of the cell membrane is sufficiently reduced and the characteristics of the entire living tissue can be fully obtained, or a frequency in a band with a great variation in a case where a variation in living body impedance is indicated, as shown in FIG. 22A) can be chosen for the detection high-frequency output. For example, when the living body impedance Z varies, as shown in FIG. 22A, information on the variation of the living tissue condition can be detected at a frequency in a band with a great variation of impedance Z.

It is possible to provide a dynamic variation between frequencies fp1 and fp2 of detection high-frequency output, as in a modification shown in FIG. 22B. Frequency characteristics may be obtained during the dynamic variation, thereby to obtain more detailed living body information.

The structure of the controller 214 is simplified because of the output at the same timing. In addition, the living tissue condition can be detected in real time. Since the treatment and detection are performed by using the same electrode of the monopolar treatment device 203, the living tissue condition for the treatment site can be exactly detected.

The order of arrangement of the output synthesizer 210 and amplifiers in the present embodiment is shown by way of example. It is possible to synthesize outputs at low level and then amplify the synthesized output. Furthermore, control with higher precision can be performed by providing means for detecting the type of treatment device connected to the cautery power supply 202 of the present embodiment.

FIGS. 23A and 23B show a sixth embodiment of the invention. This embodiment differs from the fifth embodiment (see FIGS. 19 to 22A) in that separate positive (+) terminals are provided for the treatment frequency and detection frequency.

Specifically, in the present embodiment, an insulating member 221 of the treatment device 203 is provided with a positive (+) electrode 222 for treatment high-frequency output and a positive (+) electrode 223 for detection high-frequency output, which are situated adjacent to each other. A negative (−) electrode 224 is commonly used for treatment and detection.

The positive (+) electrode 223 for detection high-frequency output is connected to a current detector 225 and a voltage detector 226. The current detector 225 is connected to a tissue condition detector 213 via a filter 227, and the voltage detector 226 is connected to the tissue condition detector 213 via a filter 228.

The above-described structure can bring about the following advantages. The treatment frequency differs from the detection frequency. Thus, the amount of noise contained in data can be reduced more easily by separating the detection frequency, than in the case where signals with the same frequency are used.

A frequency suitable for treatment (e.g. a frequency with which a high output can be obtained at a relatively low cost) can be chosen for the treatment. A frequency suitable for detection (e.g. a frequency with which the impedance of the cell membrane is sufficiently reduced and the characteristics of the entire living tissue can be fully obtained) can be chosen for the detection. In addition, the tissue condition can be detected in real time.

In this embodiment, in particular, energy of treatment frequency does not enter the current detector 225. With use of simple filters, the structure of the current detector 225 can be simplified.

Separate positive (+) terminals of the treatment device, which are arranged close to each other, may be provided for the treatment and the detection, as in the present embodiment. However, a common positive (+) electrode 229 may be used, as shown in FIG. 23B. Accordingly, a treatment device having separate electrodes for treatment and detection and a treatment device having a common electrode therefore may be used.

Figure 24:
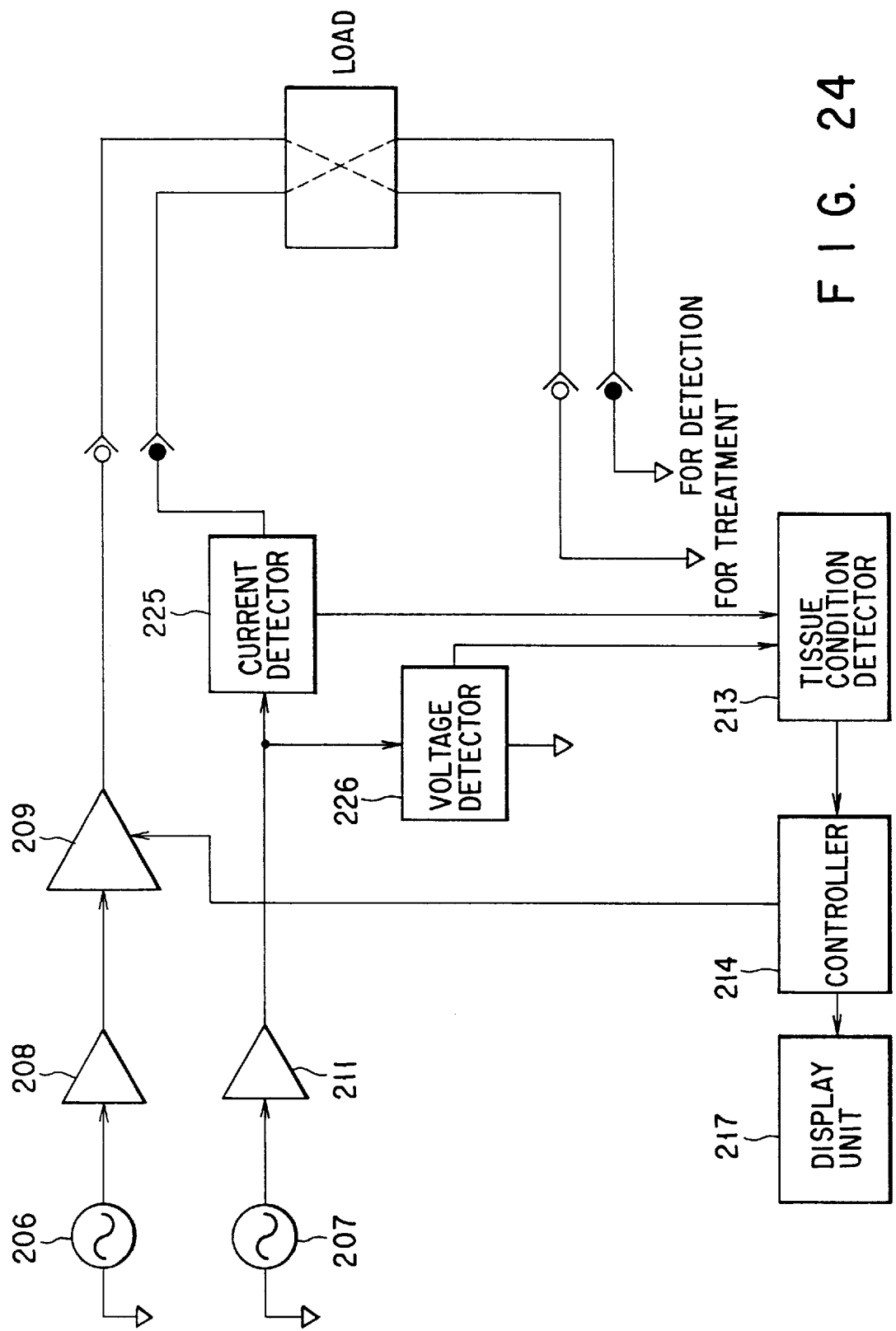
FIG. 24 schematically shows the structure of a main part of an electrosurgery apparatus according to a seventh embodiment of the invention.

FIG. 24 shows a seventh embodiment of the present invention. In this embodiment, the circuit for treatment and the circuit for detection in the sixth embodiment (see FIGS. 23A and 23B) are completely separated from the ground GND.

The above-described structure can bring about the following advantages. The treatment frequency differs from the detection frequency. Thus, the amount of noise contained in data can be reduced more easily by separating the detection frequency, than in the case where signals with the same frequency are used.

Moreover, a frequency suitable for treatment (e.g. a frequency with which a high output can be obtained at a relatively low cost) can be chosen for the treatment. A frequency suitable for detection (e.g. a frequency with which the impedance of the cell membrane is sufficiently reduced and the characteristics of the entire living tissue can be fully obtained) can be chosen for the detection. In addition, the tissue condition can be detected in real time.

In the present embodiment, in particular, the circuit for detection is completely separated from the circuit for treatment, the precision in detection is enhanced and the possibility of noise occurring due to energy of treatment frequency is very low.

Figure 25:
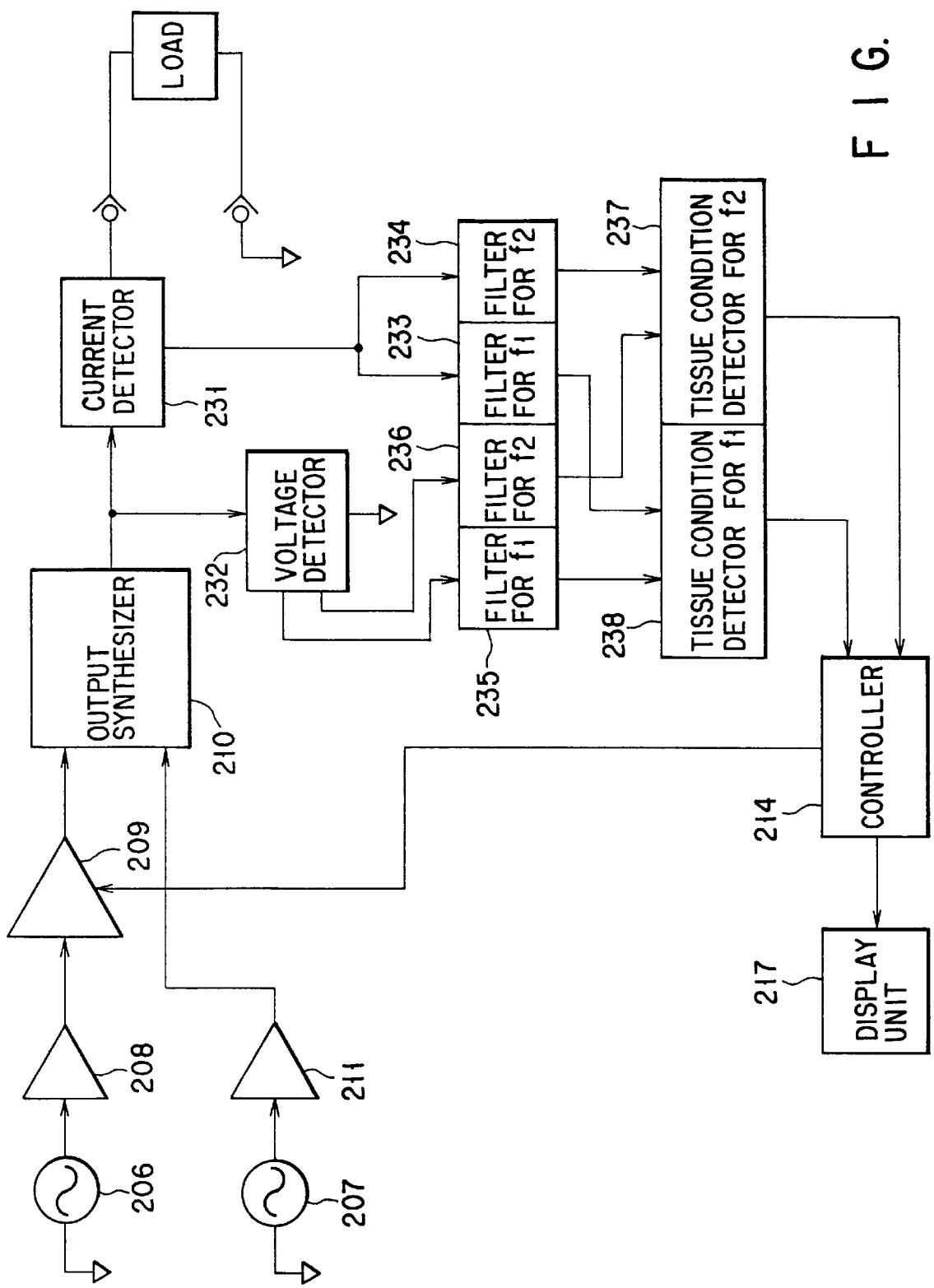
FIG. 25 schematically shows the structure of a main part of an electrosurgery apparatus according to an eighth embodiment of the invention.

FIG. 25 shows an eighth embodiment of the present invention. In this embodiment, the tissue condition is detected by using treatment frequency f1 and detection frequency f2.

In this embodiment, a current detector 231 is provided with a filter 233 for f1 (hereinafter referred to as "f1 filter") and a filter 234 for f2 (hereinafter "f2 filter"). Similarly, a voltage detector 232 is provided with an f1 filter 235 and an f2 filter 236. The two f1 filters 233 and 235 are connected to a tissue condition detector (living body information detection means) 238 for f1, and the two f2 filters 234 and 236 are connected to a tissue condition detector (living body information detection means) 237 for f2.

The above-described structure can bring about the following advantages. The treatment frequency differs from the detection frequency. Thus, the amount of noise contained in data can be reduced more easily by separating the detection frequency, than in the case where signals with the same frequency are used.

Moreover, a frequency suitable for treatment (e.g. a frequency with which a high output can be obtained at a relatively low cost) can be chosen for the treatment. A frequency suitable for detection (e.g. a frequency with which the impedance of the cell membrane is sufficiently reduced and the characteristics of the entire living tissue can be fully obtained) can be chosen for the detection. In addition, the tissue condition can be detected in real time.

In this embodiment, in particular, control can be achieved on the basis of total detection characteristics obtained at frequencies f1 and f2. For example, the water content in extracellular fluid and the protein denaturing condition are confirmed at frequency f1, and the water content in extracellular and intracellular fluids and the protein denaturing condition are confirmed at frequency f2. Thereby, the condition of tissue can be recognized more clearly.

FIGS. 26A and 26B show a ninth embodiment of the present invention. In the ninth embodiment, as shown in FIG. 26A, an adapter 241, which is an element separate from the cautery power supply 202, is provided between the cautery power supply 202 and the monopolar treatment device 203 of the electrosurgery apparatus 201 according to the fifth embodiment (see FIGS. 19 to 22A). Electric circuits shown in FIG. 26B are built in the adapter 241.

The electric circuits within the adapter 241 comprise an output controller 242, a detection frequency oscillator 243, an output synthesizer 244, a voltage detector 245, a current detector 246, a filter 247, a tissue condition detector 248, a controller 249, and a display unit 250. In the ninth embodiment, too, the same advantages as with the fifth embodiment can be obtained.

Figure 27:
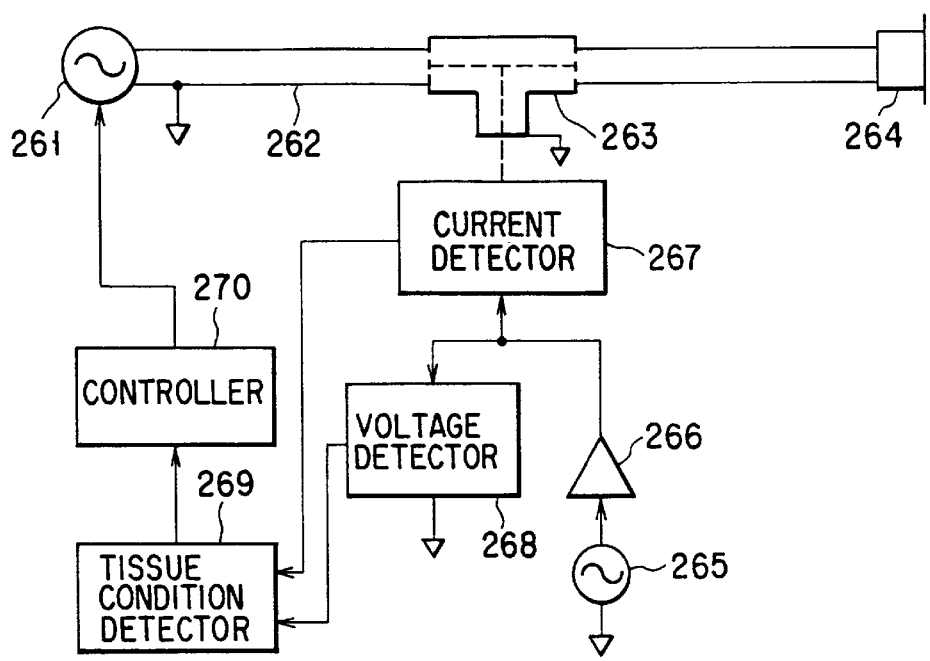
FIG. 27 schematically shows the structure of a main part of an electrosurgery apparatus according to a tenth embodiment of the invention.

FIG. 27 shows a tenth embodiment of the invention. In the tenth embodiment, a detection frequency is superimposed on an output from a coaxial output type treatment frequency oscillator 261. In general, the frequency of coaxial output treatment energy is not lower than a microwave band (300 MHz or more). On the other hand, a lower frequency, which can be generated by a simpler circuit, is used for detection. However, these frequencies are not limited and can be freely chosen.

In this embodiment, one end portion of a coaxial cable 262 is connected to the treatment frequency oscillator 261. A three-way connector 263 is provided midway along the coaxial cable 262. The other end portion of the coaxial cable 262 is connected to a coaxial connector 264.

Reference numeral 265 denotes a detection frequency oscillator; 266 an amplifier; 267 a current detector 267; 268 a voltage detector; 269 a tissue condition detector; and 270 a controller. In this embodiment, the coaxial connector 264 connected at one end to the three-way connector 263 for frequency synthesis is connected at the other end to a treatment probe (not shown) over a coaxial cable serving as transmission cable.

The above-described structure can bring about the following advantages. The treatment frequency differs from the detection frequency. Thus, the amount of noise contained in data can be reduced more easily by separating the detection frequency, than in the case where signals with the same frequency are used.

Moreover, a frequency suitable for treatment can be chosen for the treatment. A frequency suitable for detection (e.g. a frequency with which the impedance of the cell membrane is sufficiently reduced and the characteristics of the entire living tissue can be fully obtained) can be chosen for the detection. In addition, the tissue condition can be detected in real time.

In this embodiment, in particular, a treatment output is supplied via the coaxial cable 262 and a detection output is supplied as a feeder output. In this embodiment, the three-way connector 263 is used for frequency synthesis. However, the method of synthesis is not limited to this. The cable may be directly processed for synthesis.

Figure 28:
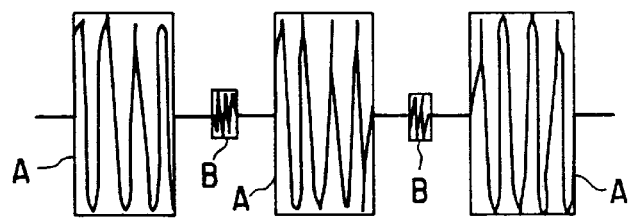
FIG. 28 schematically shows the structure of a main part of an eleventh embodiment of the invention.

FIG. 28 shows an eleventh embodiment of the invention. In this embodiment, when a treatment output A is supplied intermittently, a detection output is B is supplied while the treatment output is turned off. Thereby, the tissue condition is detected.

With this structure, the following advantages can be obtained. Noise appearing on the detection signal is reduced. Since the natural tissue condition with no application of treatment energy can be detected, the detection result is not influenced by the magnitude of treatment energy.

Figure 29:
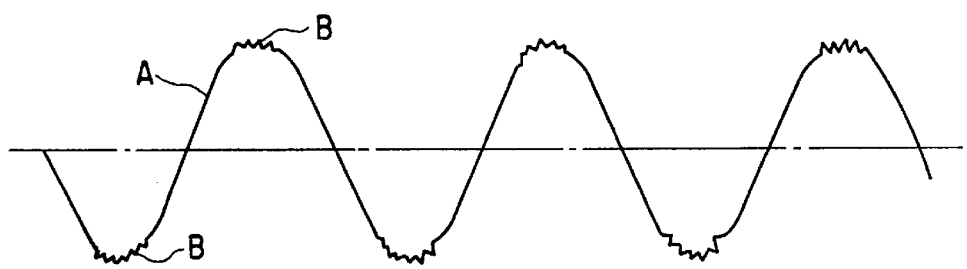
FIG. 29 schematically shows the structure of a main part of a twelfth embodiment of the invention.

FIG. 29 shows a twelfth embodiment of the invention. In this embodiment, a detection frequency B is superimposed on peak components of a treatment frequency wave A, thereby to detect the tissue condition.

This structure can bring about the following advantages. A detection signal can be obtained when the direction of an electric field applied to the living tissue is reversed. The state of polarization can be understood, and a higher-level control can be achieved.

Figure 30:
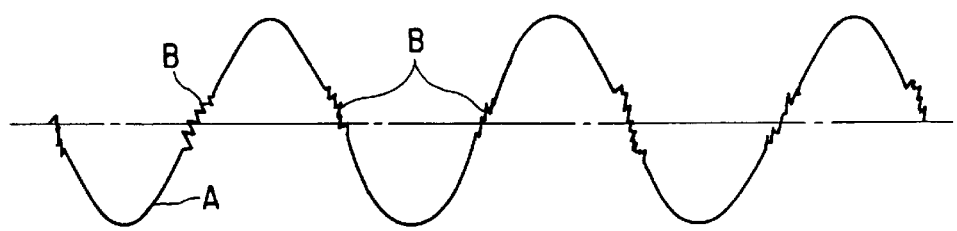
FIG. 30 schematically shows the structure of a main part of a 13th embodiment of the invention.

FIG. 30 shows a 13th embodiment of the present invention. In this embodiment, a detection frequency B is superimposed on those portions of a treatment frequency wave A, which are close to zero points of output voltage. Thereby, the tissue condition is detected.

With the abovestructure, the following advantages can be obtained. The detection can be performed with little influence by treatment energy (or treatment electric field). The detection is performed while the treatment energy is being output. Even when the treatment energy is output intermittently, the detection can be performed while the energy is being output.

FIG. 31 shows a 14th embodiment of the invention. In this embodiment, a coil 291 is substituted for a resistor in a current detector of a constant current controller 284. The coil 291 is connected to the constant current controller 284 via an LPF (low-pass filter) 292. A gain control is performed to make the current constant.

FIGS. 32, 33A and 33B show a 15th embodiment of the present invention. In this embodiment, as shown in FIG. 32, a plurality of oscillation frequency sources are provided within an electric scalpel apparatus 301, and respective frequency components can be mixed.

Specifically, the electric scalpel apparatus 301 of this embodiment comprises an adjusting dial 302 for a frequency component f1 of a first oscillation frequency source, an adjusting dial 303 for a frequency component f2 of a second oscillation frequency source, an f1 component display unit 304, and an f2 component display unit 305.

A mixing circuit provided within the electric scalpel apparatus 301 of this embodiment comprises an adder circuit 306 shown in FIG. 33A. A treatment waveform of a desired shape can be formed by the adder circuit 306, shown in FIG. 33B, by controlling the f1 adjusting dial 302 and f2 adjusting dial 303 of the electric scalpel apparatus 301.

With the above structure, the waveform can be finely adjusted according to the user's wish, and various treatment waveforms can be obtained by simple operations. Thus, the cutting performance of the electric scalpel 301 can be finely adjusted.

FIGS. 34A to 35E show a 16th embodiment of the present invention. In this embodiment, when information on living tissue impedance Z is obtained while a bipolar electric scalpel apparatus shown in FIG. 34A is producing an output, a dynamic impedance is obtained by dynamically varying frequency characteristics of a signal source.

A cautery power supply 321 of the electric scalpel apparatus of this embodiment comprises an oscillation source 322 for generating a high-frequency output; a pulse width generator 323; a switching amplifier 324; a variable power supply 325; a controller 326; a setting unit 327; an output transformer 328; a voltage detector 329; and a current detector 330. The apparatus of this embodiment has a function of freely varying a high-frequency output waveform by means of these electric circuits.

In general, even if the value of power of electric scalpel output is unchanged, a difference in high-frequency output waveform varies an influence upon the living tissue and also varies a detection result for obtaining information on impedance Z in a case where the living tissue is treated as a load. For example, a first output waveform shown in FIG. 34B and a second output waveform shown in FIG. 34C act differently upon the living tissue even if the area of the action of the waveforms is equal. In this case, the frequency spectrum of the first output waveform shown in FIG. 34B includes a greater number of high-frequency components which are close to impulses. In addition, the first output waveform shown in FIG. 34B has higher voltage wave values and is easier to discharge.

Due to a difference in high-frequency output waveform, output characteristics (output impedance) also vary, and cutting and coagulation performances change. Specifically, the coagulation performance is enhanced with the first output waveform shown in FIG. 34B, and the cutting performance is enhanced with the second output waveform shown in FIG. 34C.

In the electric scalpel apparatus of this embodiment, while the value of output power of the electrical scalpel apparatus applied to the living tissue is kept constant, as shown in FIG. 35B, the voltage and frequency are dynamically varied. In accordance with a variation in output impedance Z at this time, the output is controlled. For example, when the voltage and frequency characteristics are dynamically varied (with simple structure) with equal power (i.e. with equal cautery energy), the first output waveform shown in FIG. 34B and the second output waveform shown in FIG. 34C are alternately or successively varied. FIG. 35A is a characteristic graph showing a variation in output waveform of the electric scalpel apparatus according to the 16th embodiment. FIG. 35B is a characteristic graph of an output of the electric scalpel. FIG. 35C is a characteristic graph of an R component current of the electric scalpel. FIG. 35D is a characteristic graph of a C component current of the electric scalpel. FIG. 35E is a characteristic graph showing a variation in C component current of the electric scalpel.

With the above-described structure, the electrical characteristics of the treatment unit can be obtained more exactly.

Figure 36A:
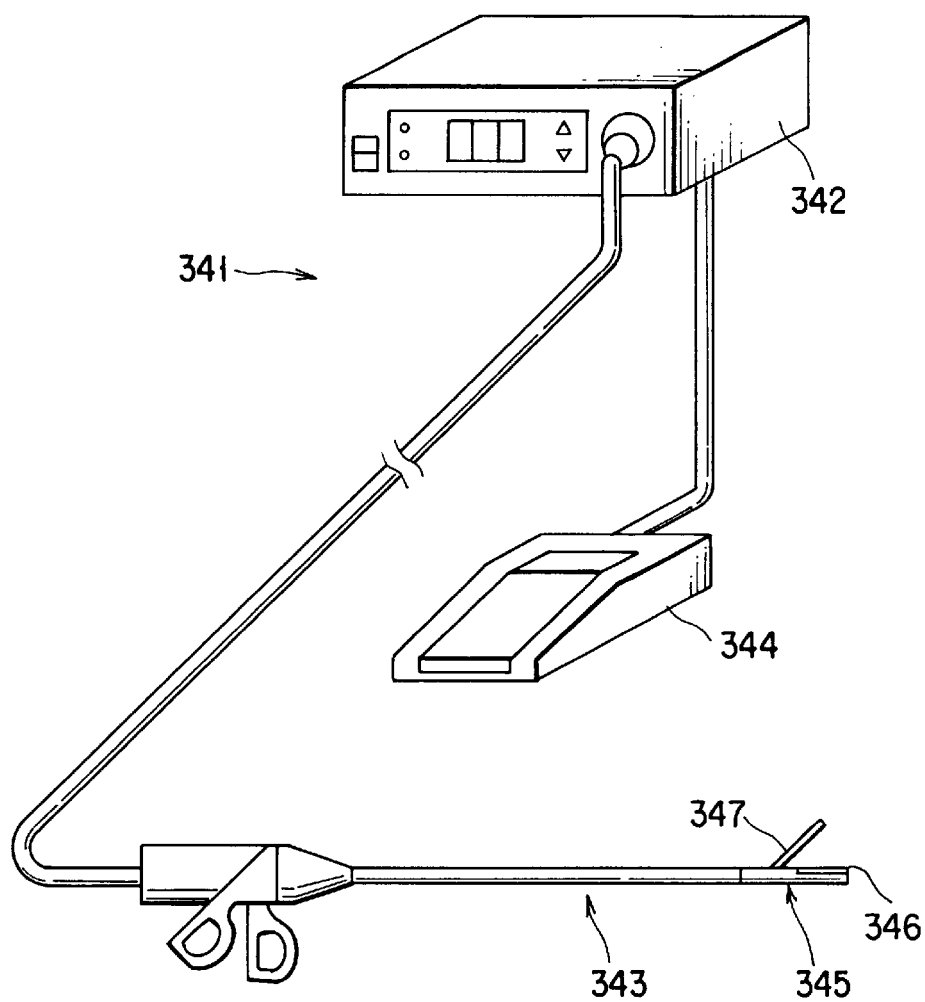
FIG. 36A is a perspective view of an electrosurgery apparatus according to a 17th embodiment of the invention.
Figure 36B:
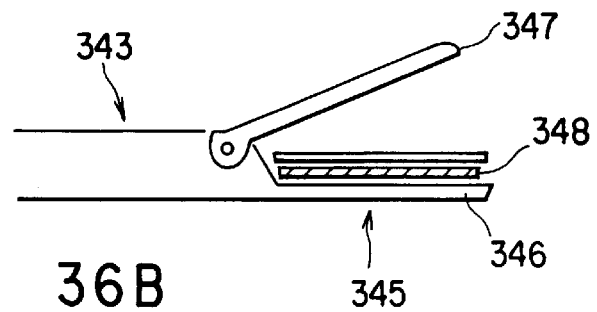
FIG. 36B is a side view of a treatment unit of the electrosurgery apparatus according to the 17th embodiment.

FIGS. 36A, 36B and 37A show a 17th embodiment of the present invention. In this embodiment, while the condition of a treatment site is being monitored on the basis of ultrasonic oscillation or ultrasonic acoustic impedance, a treatment is performed by means of electric scalpel energy. As is shown in FIG. 36A, an electrosurgery apparatus 341 of this embodiment is used for an endoscopic surgical operation. The electrosurgery apparatus 341 comprises a treatment device 343 capable of holding a living tissue; an ultrasonic oscillator 348 to be used in contact with the treatment site; and controllable electric scalpel energy supply means or a cautery power supply 342, as shown in FIG. 37A.

The cautery power supply 342 comprises an ultrasonic oscillator (examination output generating means) 349, a high-frequency (or RF (radio-frequency)) output circuit (energy supply means) 350, and a controller 351. As is shown in FIG. 36B, the treatment device 343 has a treatment section 345 at its distal end portion. The treatment section 345 is provided with two bipolar electrodes 347 and 346, one of which is provided with a piezoelectric element of the ultrasonic oscillator (examination output supply means) 348.

At the time of treatment, a mechanical/acoustic impedance is detected by ultrasonic waves before electric scalpel energy is output, thereby examining the hardness of a living tissue to be treated. Then, electric scalpel energy is supplied while monitoring the living tissue or in a time-division manner. After the impedance has reached a predetermined value, the output of electric scalpel energy is stopped or varied.

In a surgical (open) operation, the operator performs the treatment while examining the treatment site by the touch sense of his/her finger. On the other hand, in an endoscopic operation, the operator cannot directly obtain the touch sense. Thus, the detection of mechanical/acoustic impedance can assist the operator who cannot obtain the touch sense.

In the above structure, while the condition of the interior of the living tissue is being monitored, the treatment can be performed (excessive cautery or deficient cautery can be prevented). Since the ultrasonic oscillation is provided at the same time, adhesion of the living tissue to the treatment section can be prevented. The combination of the oscillation and the use of the electric scalpel can achieve uniform, exact adhesion (of blood vessel, etc.). Thus, the treatment can be controlled while confirming the condition of the treatment site.

Since the ultrasonic oscillator 348 is provided on the treatment section (holding section) 345 of treatment device 343, the condition of the living tissue can be directly measured and the length of the treatment device 343 can be freely adjusted.

Figure 38A:
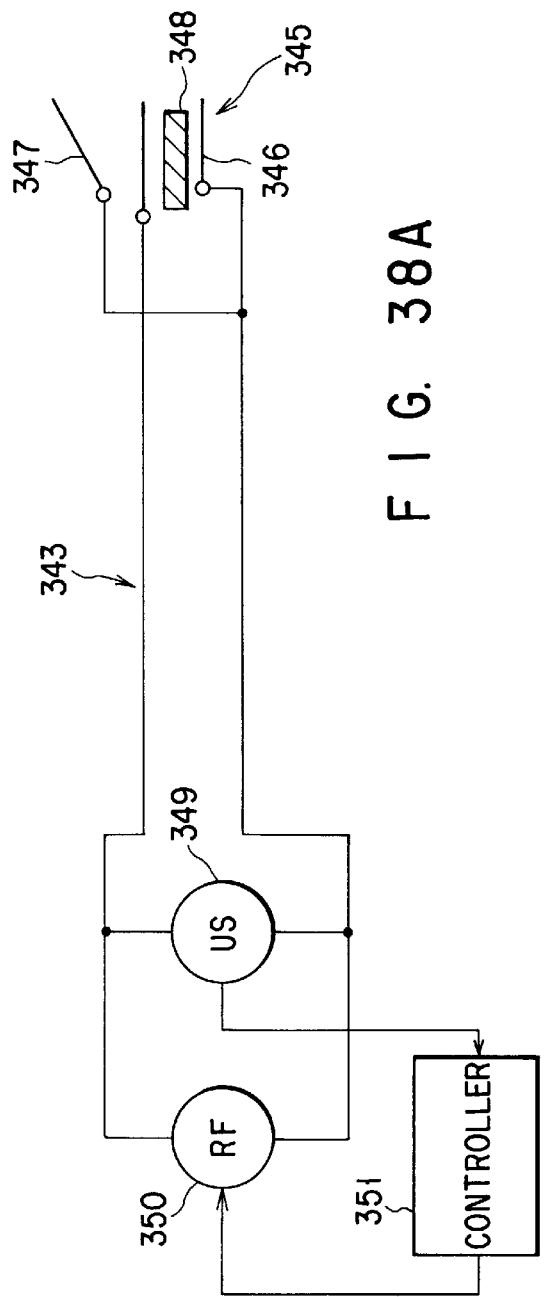
FIG. 38A schematically shows the structure of a second modification of the 17th embodiment.

The structure of the 17th embodiment may be modified as shown in FIG. 37B (first modification) or in FIG. 38A (second modification). In these modifications, the advantages as with the 17th embodiment can be obtained.

Figure 38B:
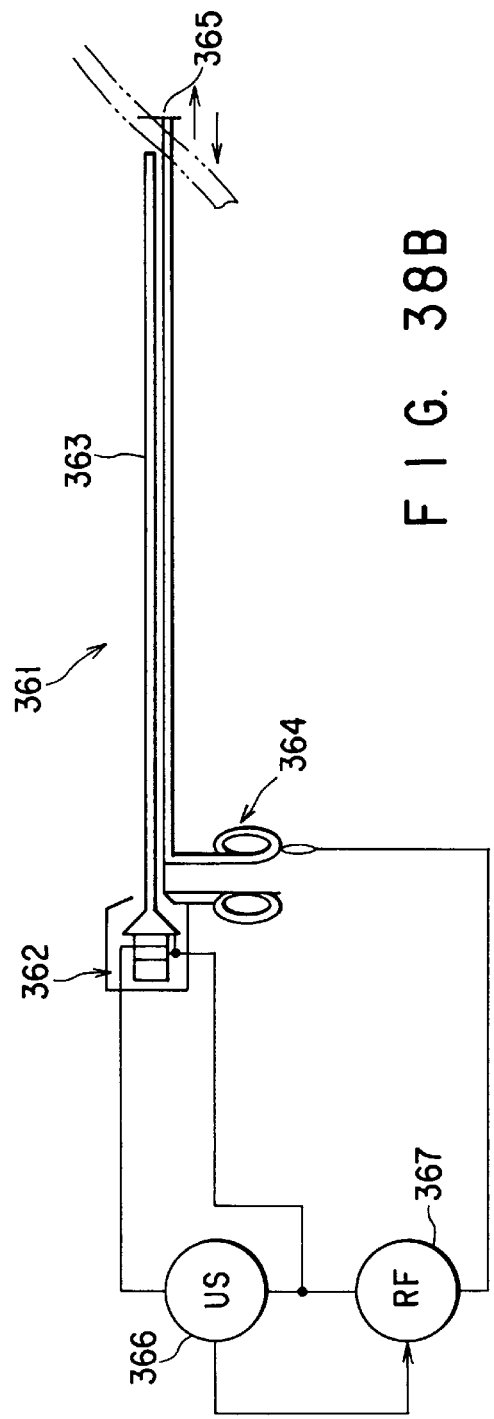
FIG. 38B schematically shows the structure of a third modification of the 17th embodiment.

FIG. 38B shows a third modification of the 17th embodiment. A Langevin type high-energy ultrasonic oscillator 362 is provided on a handpiece section 361. Thus, a bipolar treatment device capable of performing ultrasonic treatment is obtained. In FIG. 38B, reference numeral 363 denotes an oscillation transmission member of the ultrasonic oscillator 162; 364 an operational handle for axially moving a clamping member 365 provided at a distal end of the handpiece section 361; 366 an ultrasonic oscillator; and 367 a high-frequency output circuit.

Figure 39:
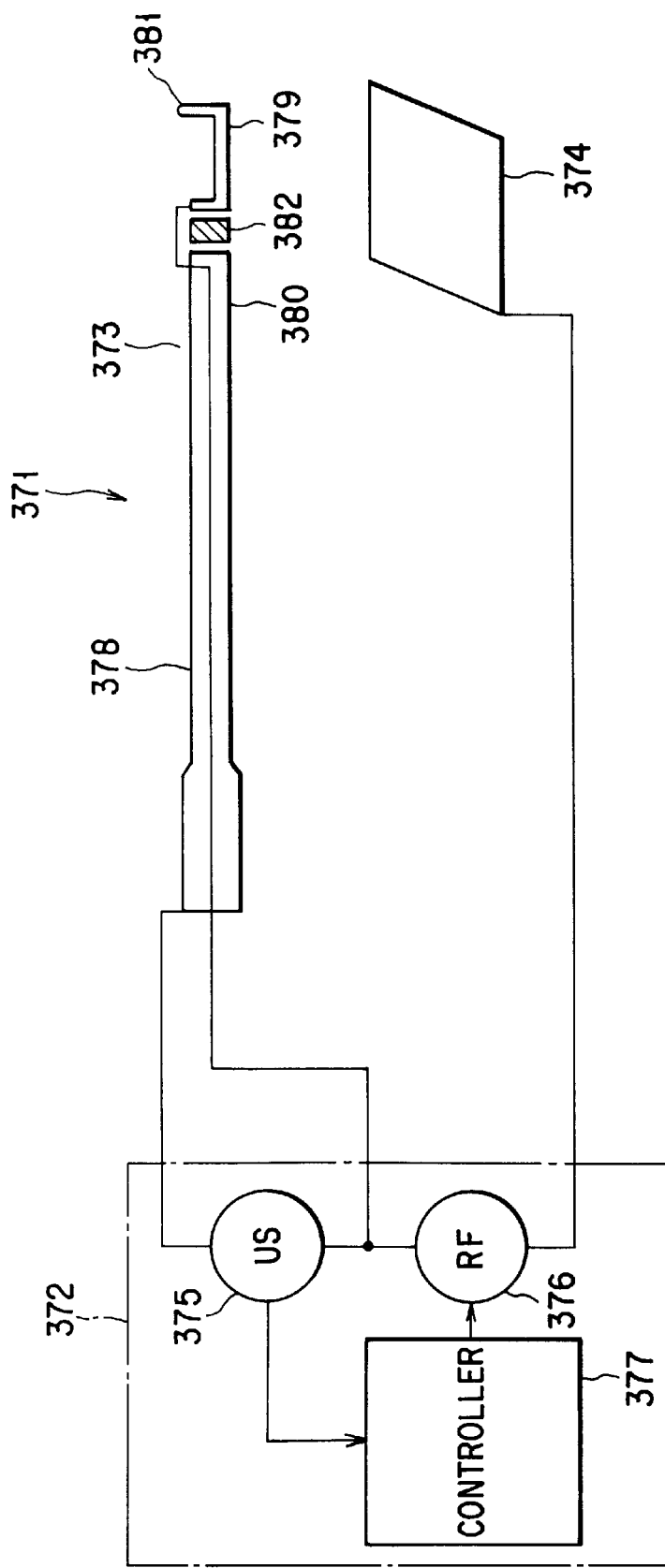
FIG. 39 schematically shows the structure of an electrosurgery apparatus according to a 18th embodiment of the invention.

FIG. 39 shows an 18th embodiment of the present invention. An electrosurgery apparatus 371 of this embodiment comprises a cautery power supply 372, a hook type treatment device 373, and a counter electrode plate 374. The cautery power supply 372 includes an ultrasonic oscillator (examination output generating means) 375, a high-frequency output circuit (energy supply means) 376 and a controller 377.

The treatment device 373 has an elongated treatment device body 378. A distal end portion of the treatment device body 378 is provided with two electrodes 379 and 380. The first electrode 379 provided on the distal end side has a hook portion 381 for hooking the living tissue. In addition, an ultrasonic oscillation element (living body information detection means) 382 for acquiring living body information of the living tissue to be treated is provided between the first electrode 379 and the second electrode 280 situated in rear of the first electrode 379.

The operation of the above structure will now be described. When the electrosurgery apparatus 371 of this embodiment is used, the living tissue is hooked by the hook portion 381 of first electrode 379 of treatment device body 378. In this state, the living tissue is cauterized by a high-frequency output. During the treatment, the ultrasonic oscillator 375 is driven and the ultrasonic oscillation element 382 provided between the first electrode 379 and second electrode 380 applies detection ultrasonic oscillation to the living tissue. In this case, an ultrasonic signal reflected by the living tissue is detected by the ultrasonic oscillator 382. Living body information on the living tissue is obtained on the basis of a variation in the ultrasonic signal detected by the ultrasonic oscillation element 382. In addition, based on the living body information, the high-frequency output circuit 376 is controlled and the high-frequency output is controlled.

In the above structure, the ultrasonic oscillation element 382 is provided between the first electrode 379 and second electrode 380. While the living tissue to be treated is cauterized by the high-frequency output, the living body information on the living tissue is acquired on the basis of the detection data obtained by the ultrasonic oscillation element 382. Therefore, the treatment condition of the living tissue regarded as a load can exactly be detected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. An electrosurgery apparatus including an electric scalpel having a treatment section for treating a living tissue, and an energy supply for supplying treatment energy to the treatment section, wherein the living tissue is treated by the treatment section while the treatment energy is being supplied to the treatment section, the apparatus further comprising:
variation detection means for detecting a variation in condition of the energy supplied to the treatment section while the living tissue is being treated, said variation detection means including means for measuring an impedance in the living tissue while an output is being delivered from the electric scalpel, and detection means for detecting a variation range of the measured impedance; and
living body information detection means for acquiring living body information on the living tissue to be treated, on the basis of detection data obtained by said variation detection means, said living body information detection means including output control means for effecting one of stopping and reducing of the output of the electric scalpel, while the output is being supplied, when the detection means detects the variation range of the measured impedance per unit time which is greater than the variation range of the impedance per unit time which is measured in a predetermined time period lust after the treatment section starts to treat the living tissue.

2. An electrosurgery apparatus comprising:
a treatment device having a treatment section for treating a living tissue;
an energy supply for supplying treatment energy to the treatment section;
examination output generating means for generating an examination output for examining the state of the living tissue;
examination output supply means for supplying the examination output, which is generated by the examination output generating means, to the treatment section, such that the examination output and the treatment energy are superimposed together and are applied to the treatment section at the same time;

wherein the living tissue is treated by the treatment section while both of the treatment energy and the examination output are concurrently supplied to the treatment section; and living body information detection means for detecting a variation in the examination output and acquiring living body information on the living tissue to be treated, on the basis of the detected variation in the examination output.

3. The apparatus according to claim 2, wherein:

said treatment section comprises a treatment electrode, said energy supply comprises an electric energy supply section for supplying treatment electric energy to the treatment electrode, said examination output generating means comprises examination signal generating means for generating an examination signal having a frequency different from a frequency of the treatment electric energy supplied to the treatment electrode, said examination output supply means comprises examination signal supply means for supplying the examination signal generated by the examination signal generating means to the treatment electrode at the same time that the treatment electric energy is supplied to the treatment electrode, and said living body information detection means detects a variation in the examination signal and acquires the living body information on the living tissue to be treated, on the basis of the detected variation in the examination signal.

4. The apparatus according to claim 1, wherein said energy supply comprises:

a plurality of high-frequency oscillation sources for outputting high-frequency outputs with different oscillation frequencies to the electric scalpel; and a mixing circuit for mixing the high-frequency outputs with the different oscillation frequencies.

5. The apparatus according to claim 1, wherein said energy supply comprises:

an oscillation source for supplying a high-frequency output to the electric scalpel;

an amplifier;

a power supply unit for supplying power to the amplifier;

a detection circuit for obtaining impedance information when said living tissue is regarded as a load; and output control means for controlling an output of the electric scalpel in accordance with a variation in the impedance information which is obtained when one of a voltage and a frequency is dynamically varied while a power applied to the living tissue is kept constant.

6. The apparatus according to claim 1, further comprising:

output control means for controlling an output of the treatment section of the electric scalpel on the basis of the living body information obtained by the living body information detection means.

7. The apparatus according to claim 1, wherein:

said electric scalpel has a plurality of treatment electrodes for treating the living tissue, said energy supply comprises an electric energy supply for supplying treatment electric energy to the treatment electrodes, said variation detection means comprises means for measuring at least one of a current and a voltage between the treatment electrodes, and said detection means detects a variation in at least one of the voltage and current, and said output control means of said living body information detection means controls an output of the electric energy supply on the basis of an output signal from the detection means, with at least one of parameters including an initial value of the detected value of the detection means, a predetermined maximum value, a predetermined minimum value and a rate of change of the detected value being selected as a condition for finishing cautery.

8. The apparatus according to claim 1, wherein.

said electric scalpel has a plurality of treatment electrodes for treating the living tissue, said energy supply comprises an electric energy supply for supplying treatment electric energy to the treatment electrodes, said variation detection means comprises an impedance detection circuit for detecting an impedance between the treatment electrodes, and said output control means of said living body information detection means controls an output of the electric energy supply on the basis of an output signal from the impedance detection circuit, with a most proper one of parameters including an initial value of the detected value of the impedance detection circuit, a rate of change of the impedance, a predetermined upper limit value of the impedance and a predetermined lower limit value of the impedance being selected as a condition for finishing cautery.

9. The apparatus according to claim 1, wherein said predetermined value of impedance is calculated on the basis of a minimum value of the impedance of the living tissue, which is detected by said variation detection means after the electric scalpel begins to deliver the output.

10. The apparatus according to claim 1, wherein said treatment section comprises a treatment electrode, said energy supply comprises an electric energy supply for supplying treatment electric energy to the treatment electrode, said variation detection means includes a phase difference detection means for detecting a phase difference between an output voltage and an output current during high-frequency treatment by said treatment section, and said output control means of said living body information detection means effects said one of stopping and reducing of an output from the treatment means when a predetermined treatment finish condition for effecting said one of stopping and reducing of the output of the treatment section has been detected.

11. The apparatus according to claim 10, wherein said predetermined treatment finish condition is when a value of the detected phase difference has fallen out of a predetermined range.

12. The apparatus according to claim 10, wherein said predetermined treatment finish condition is when a rate of change of the detected phase difference has exceeded a predetermined value.

13. The apparatus according to claim 10, wherein said predetermined treatment finish condition is when a variation range of the detected phase difference has exceeded a predetermined value.

14. The apparatus according to claim 10, wherein said predetermined treatment finish condition is determined on the basis of an initial value after the treatment section begins to deliver the output.

15. A medical apparatus in which an electrosurgery apparatus for treating a living tissue is combined with an endoscope, the electrosurgery apparatus including an electric scalpel having a treatment for treating the living tissue, and an energy supply for supplying treatment energy to the treatment section, the electrosurgery apparatus comprising:
variation detection means for detecting a variation in condition of the energy supplied to the treatment section while the living tissue is being treated, said variation detection means including means for measuring an impedance in the living tissue while an output is being delivered from the electric scalpel, and detection means for detecting a variation range of the measured impedance; and living body information detection means for acquiring living body information on the living tissue to be treated, on the basis of detection data obtained by said variation detection means, said living body information detection means including output control means for effecting one of stopping and reducing of the output of the electric scalpel, while the output is being supplied, when the detection means detects the variation range of the measured impedance per unit time which is greater than the variation range of the impedance per unit time which is measured in a predetermined time period lust after the treatment section starts to treat the living tissue; and the endoscope comprising an observation section for observing an operation of the treatment section of the electric scalpel.

* * * * *